United States Patent
Yoshida

(10) Patent No.: US 10,937,207 B2
(45) Date of Patent: Mar. 2, 2021

(54) MEDICAL IMAGE DIAGNOSTIC APPARATUS, MEDICAL IMAGE PROCESSING APPARATUS, AND IMAGE PROCESSING METHOD

(71) Applicant: Canon Medical Systems Corporation, Otawara (JP)

(72) Inventor: Masaki Yoshida, Yaita (JP)

(73) Assignee: Canon Medical Systems Corporation, Otawara (JP)

( * ) Notice: Subject to any disclaimer, the term of this patent is extended or adjusted under 35 U.S.C. 154(b) by 77 days.

(21) Appl. No.: 16/275,617

(22) Filed: Feb. 14, 2019

(65) Prior Publication Data
US 2019/0259186 A1 Aug. 22, 2019

(30) Foreign Application Priority Data

Feb. 16, 2018 (JP) .............................. JP2018-025975
Feb. 13, 2019 (JP) .............................. JP2019-023127

(51) Int. Cl.
*G06T 11/00* (2006.01)
*G06T 7/11* (2017.01)
(Continued)

(52) U.S. Cl.
CPC .......... *G06T 11/005* (2013.01); *A61B 8/0866* (2013.01); *A61B 8/13* (2013.01);
(Continued)

(58) Field of Classification Search
CPC .......... G06T 11/005; G06T 7/11; G06T 11/60; G06T 2210/41; G06T 2207/10132; G06T 2207/30044; G06T 2207/10072; A61B 8/13; A61B 8/0866; A61B 8/5246; A61B 8/469; A61B 8/463
(Continued)

(56) References Cited

U.S. PATENT DOCUMENTS

2005/0090742 A1* 4/2005 Mine ..................... A61B 34/20
600/443
2012/0078102 A1 3/2012 Lee
(Continued)

FOREIGN PATENT DOCUMENTS

JP 2001-145631 5/2001
JP 2012-66069 4/2012
(Continued)

*Primary Examiner* — Congvan Tran
(74) *Attorney, Agent, or Firm* — Oblon, McClelland, Maier & Neustadt, L.L.P.

(57) ABSTRACT

According to one embodiment, a medical image diagnostic apparatus includes processing circuitry. The processing circuitry sets a viewpoint and an observation direction relative to medical image data. The processing circuitry searches for a region that satisfies a predetermined requirement from a search initiation surface set at a predetermined position farther away from the viewpoint in comparison with a non-display region in the medical image data in a direction toward the viewpoint, and calculates a drawing initiation surface based on a result of the search. The processing circuitry executes drawing processing from the drawing initiation surface in the observation direction, and generates display image data.

19 Claims, 14 Drawing Sheets

(51) Int. Cl.
*G06T 11/60* (2006.01)
*A61B 8/13* (2006.01)
*A61B 8/08* (2006.01)
*A61B 8/00* (2006.01)
*A61B 8/14* (2006.01)

(52) U.S. Cl.
CPC ............... *A61B 8/14* (2013.01); *A61B 8/461* (2013.01); *A61B 8/463* (2013.01); *A61B 8/466* (2013.01); *A61B 8/469* (2013.01); *A61B 8/483* (2013.01); *A61B 8/523* (2013.01); *A61B 8/5207* (2013.01); *A61B 8/5246* (2013.01); *G06T 7/11* (2017.01); *G06T 11/60* (2013.01); *G06T 2207/10072* (2013.01); *G06T 2207/10132* (2013.01); *G06T 2207/30044* (2013.01); *G06T 2210/41* (2013.01)

(58) Field of Classification Search
USPC .......................................................... 382/131
See application file for complete search history.

(56) References Cited

U.S. PATENT DOCUMENTS

| 2013/0235032 | A1 | 9/2013 | Kim et al. |
| 2014/0152661 | A1* | 6/2014 | Nishiura ............... A61B 90/36 345/424 |
| 2014/0343428 | A1* | 11/2014 | Tanaka ................ G01S 7/52074 600/440 |

FOREIGN PATENT DOCUMENTS

| JP | 2012-239576 | 12/2012 |
| JP | 2013-186905 | 9/2013 |
| JP | 2016-73541 | 5/2016 |

* cited by examiner

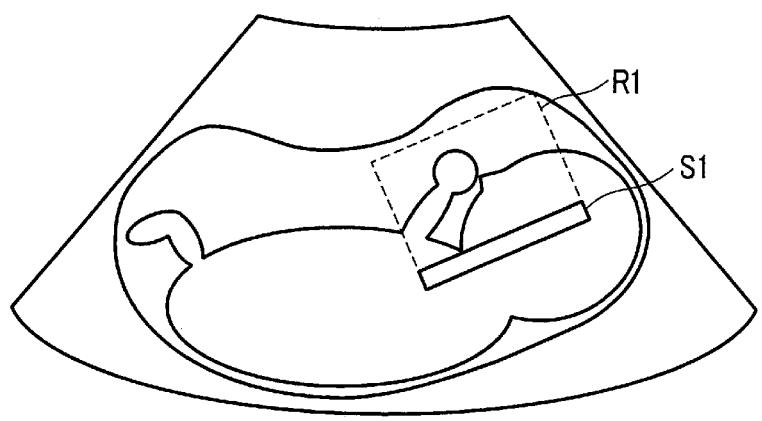
F I G. 4
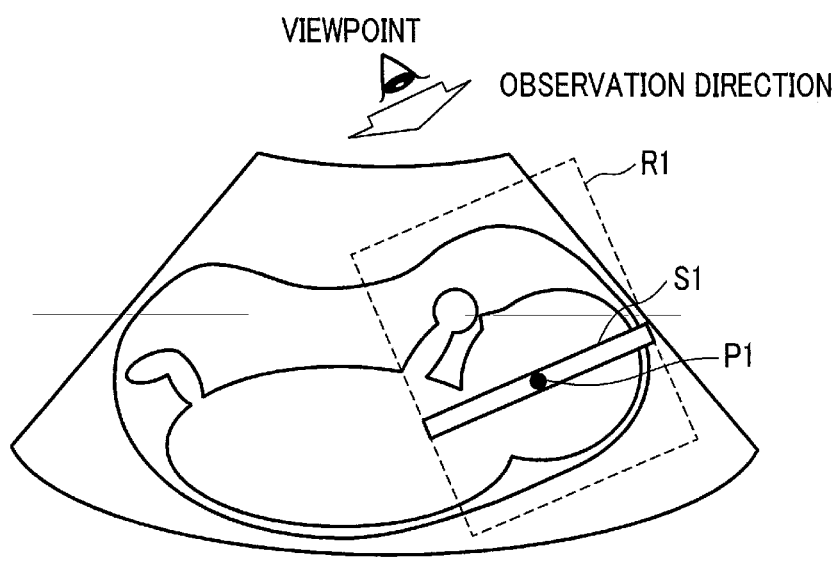
F I G. 5

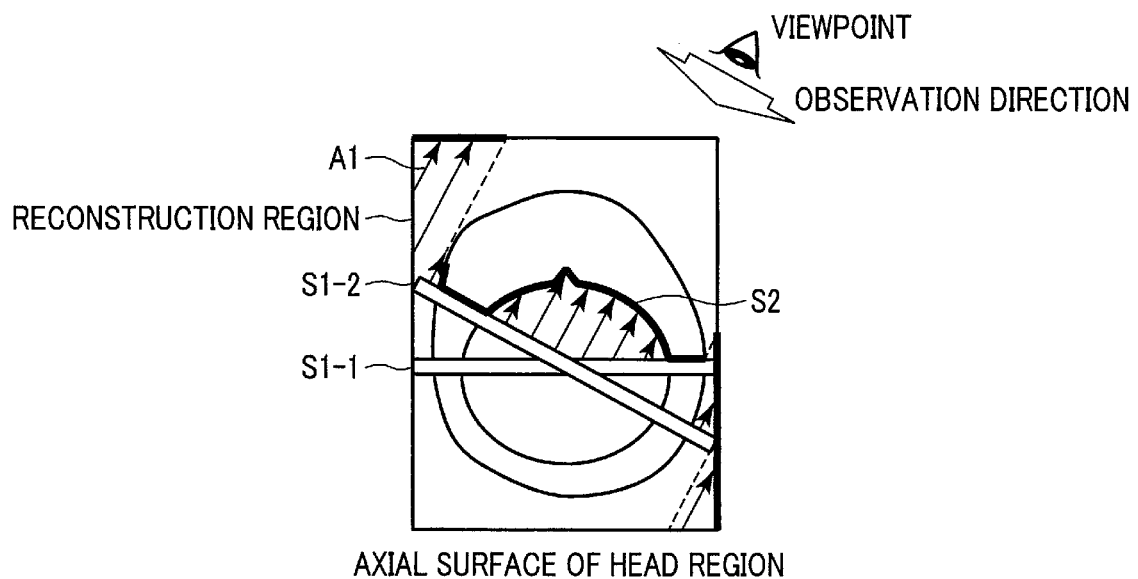
F I G. 11
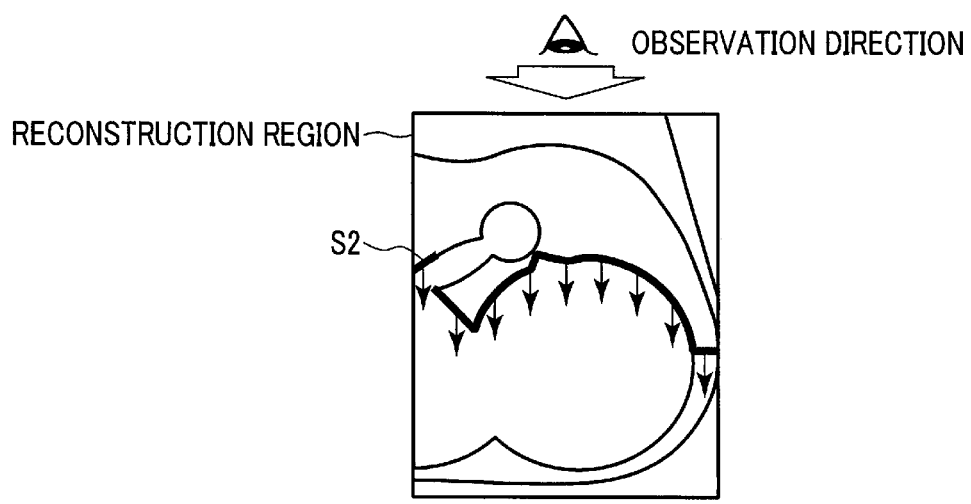
F I G. 12

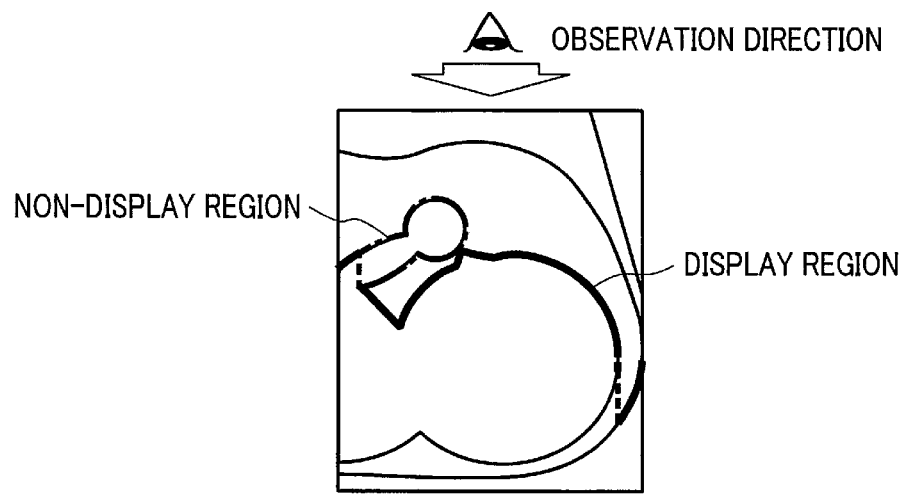
F I G. 13
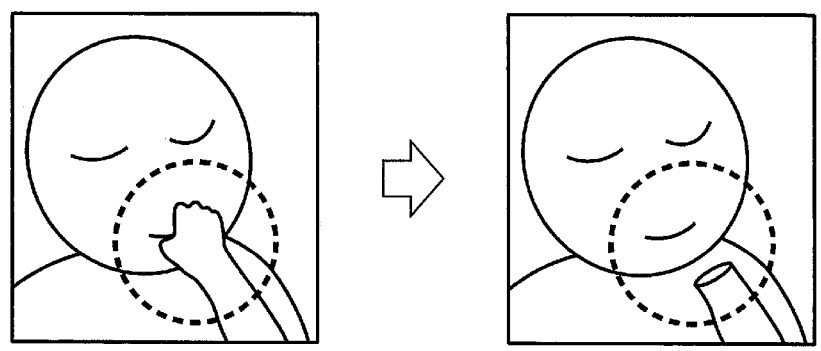
F I G. 14

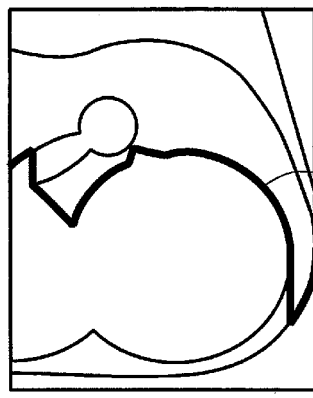
F I G. 15
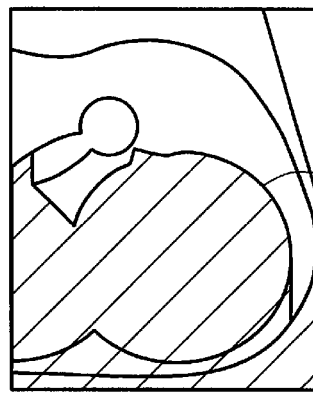
F I G. 16
F I G. 17

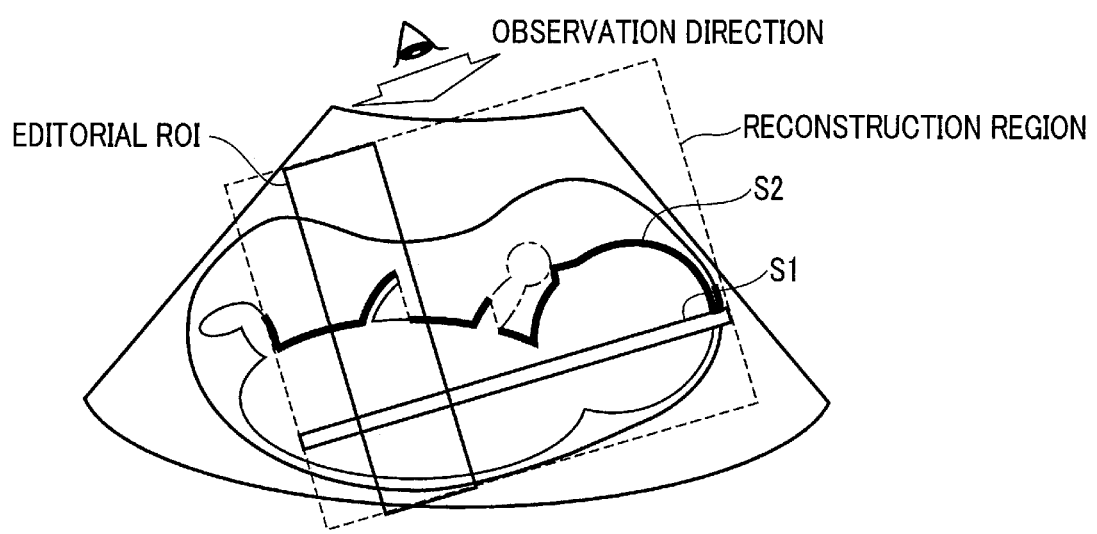
F I G. 18

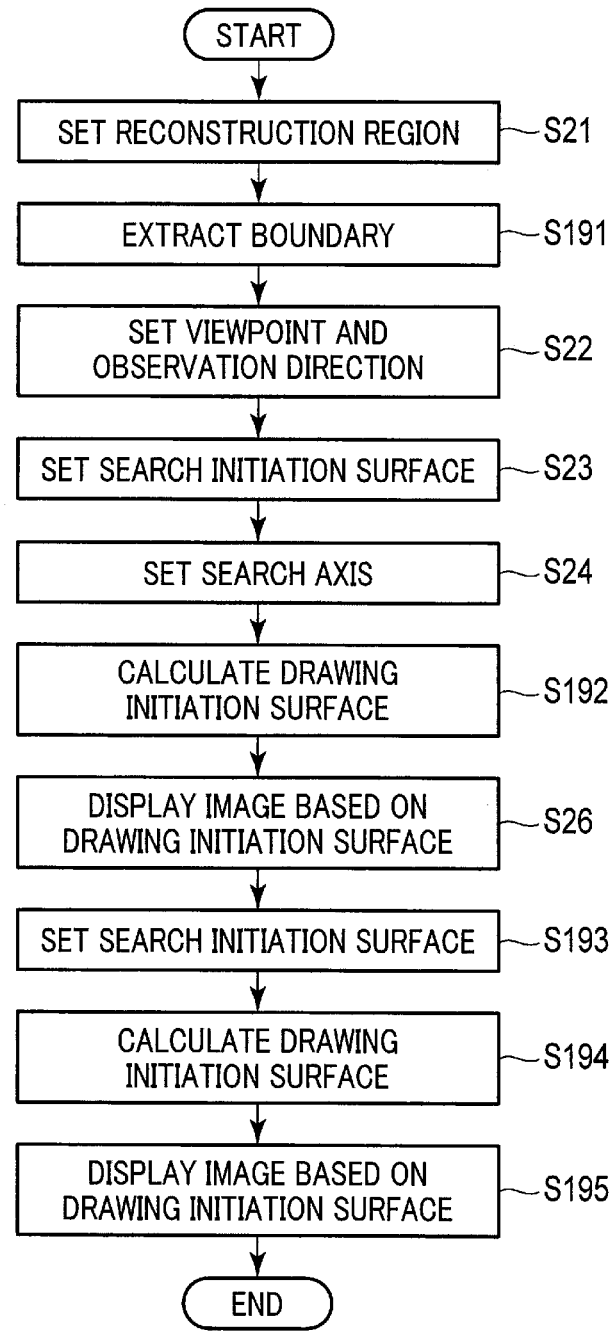
F I G. 19

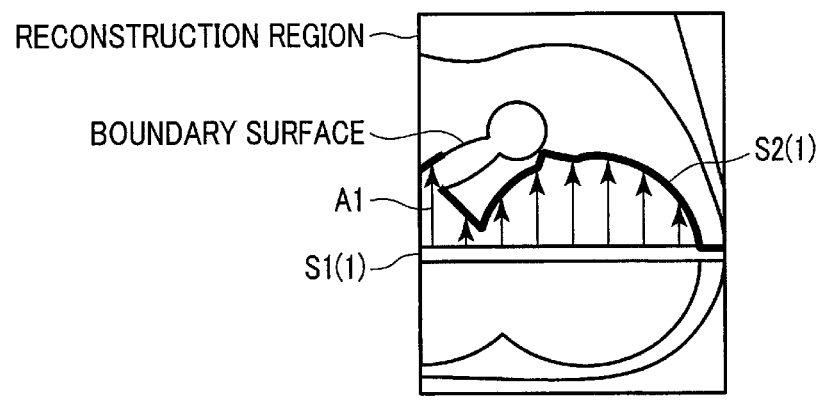
F I G. 20
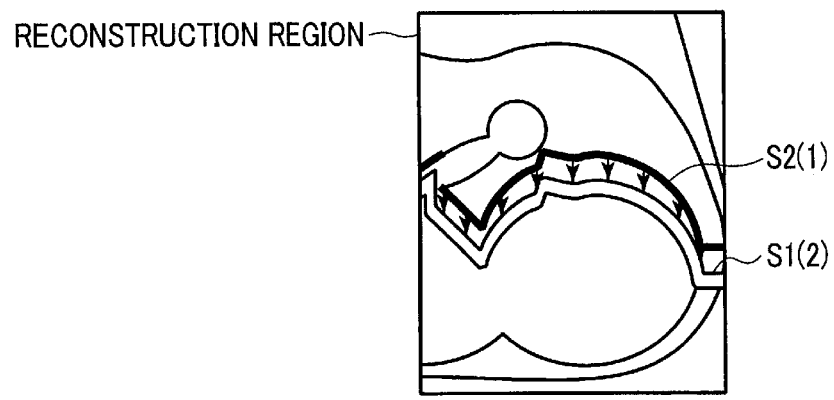
F I G. 21

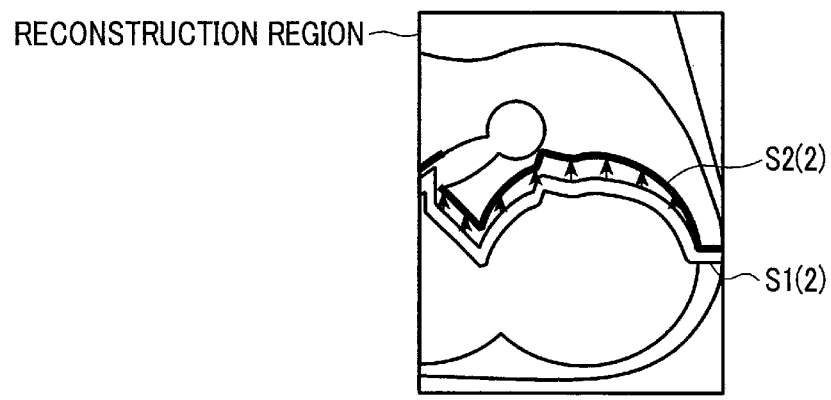
F I G. 22
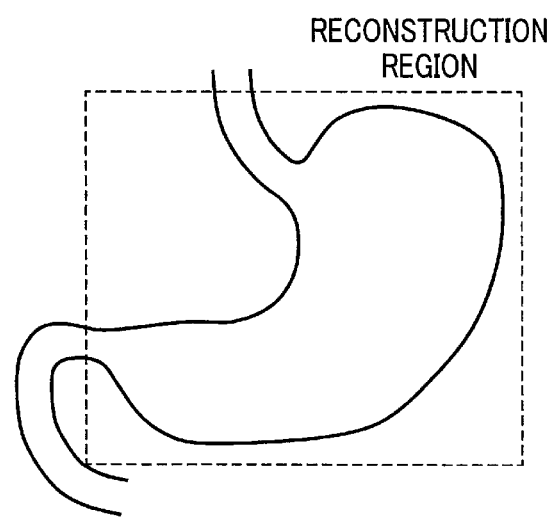
F I G. 23

MEDICAL IMAGE DIAGNOSTIC APPARATUS, MEDICAL IMAGE PROCESSING APPARATUS, AND IMAGE PROCESSING METHOD

CROSS-REFERENCE TO RELATED APPLICATIONS

This application is based upon and claims the benefit of priority from the prior Japanese Patent Application No. 2018-025975, filed Feb. 16, 2018 and No. 2019-23127, filed Feb. 13, 2019, the entire contents of both which are incorporated herein by reference.

FIELD

Embodiments described herein relate generally to a medical image diagnostic apparatus, a medical image processing apparatus, and an image processing method.

BACKGROUND

Four-dimensional image display by ultrasonic diagnostic apparatuses is already a known method for observing an affected part of a patient. In the four-dimensional image display, a reconstruction region set within an ultrasonic image is four-dimensionally reconstructed. The reconstructed data is then projected onto a screen by a projection method such as ray casting, etc. to visualize the three-dimensional form information of the affected part as a time-phase image. Via this method, the observation target can be clearly observed in comparison with a two-dimensional image. This is a great advantage, in particular, for a pregnant woman who wishes to observe a body or a face of a fetus before delivery, for example.

However, via the conventional four-dimensional image display method, the observation target is hidden if an object that obstructs the observation is placed in front of the observation target. It is possible to delete a region of the obstacle by the known region extraction algorithm, etc.; however, such a process is cumbersome, and the observation cannot be realized in real-time.

BRIEF DESCRIPTION OF THE DRAWINGS

FIG. 4 is a diagram showing a search initiation surface set by using a part of a surface constituting a reconstruction region.

FIG. 5 is a diagram showing a search initiation surface set to pass through a point in a head.

FIG. 11 is a diagram showing a drawing initiation surface calculated in a case where multiple search initiation surfaces are set.

FIG. 12 is a drawing showing rendering processing executed along an observation direction from the drawing initiation surface.

FIG. 13 is a drawing showing rendering image data in which a face region of a fetus is a display region, and an arm region is a non-display region.

FIG. 14 is a drawing showing a display example in a case where the arm region is deleted as a non-display region.

FIG. 15 is a drawing showing a tomographic image in which a surface of a display region is colored so as to be distinguishable from a non-display region.

FIG. 16 is a drawing showing a tomographic image in which a range of a display region is colored so as to be distinguishable from a non-display region.

FIG. 17 is a drawing showing a display example in a case where an arm region (non-displayed) is superimposed.

FIG. 18 is a diagram showing an editorial ROI set on a tomographic image.

FIG. 19 is a flowchart of another example of the operation when generating rendering image data by image processing circuitry shown in FIG. 1.

FIG. 20 is a diagram showing a drawing initiation surface S2 (1) calculated based on a search from a search initiation surface S1 (1).

FIG. 21 is a diagram showing a search initiation surface S1 (2) set based on the drawing initiation surface S2 (1).

FIG. 22 is a diagram showing a drawing initiation surface S2 (2) calculated based on a search from a search initiation surface S1 (2).

FIG. 23 is a diagram showing a reconstruction region set relative to a medical image including a stomach.

DETAILED DESCRIPTION

Figure 1:
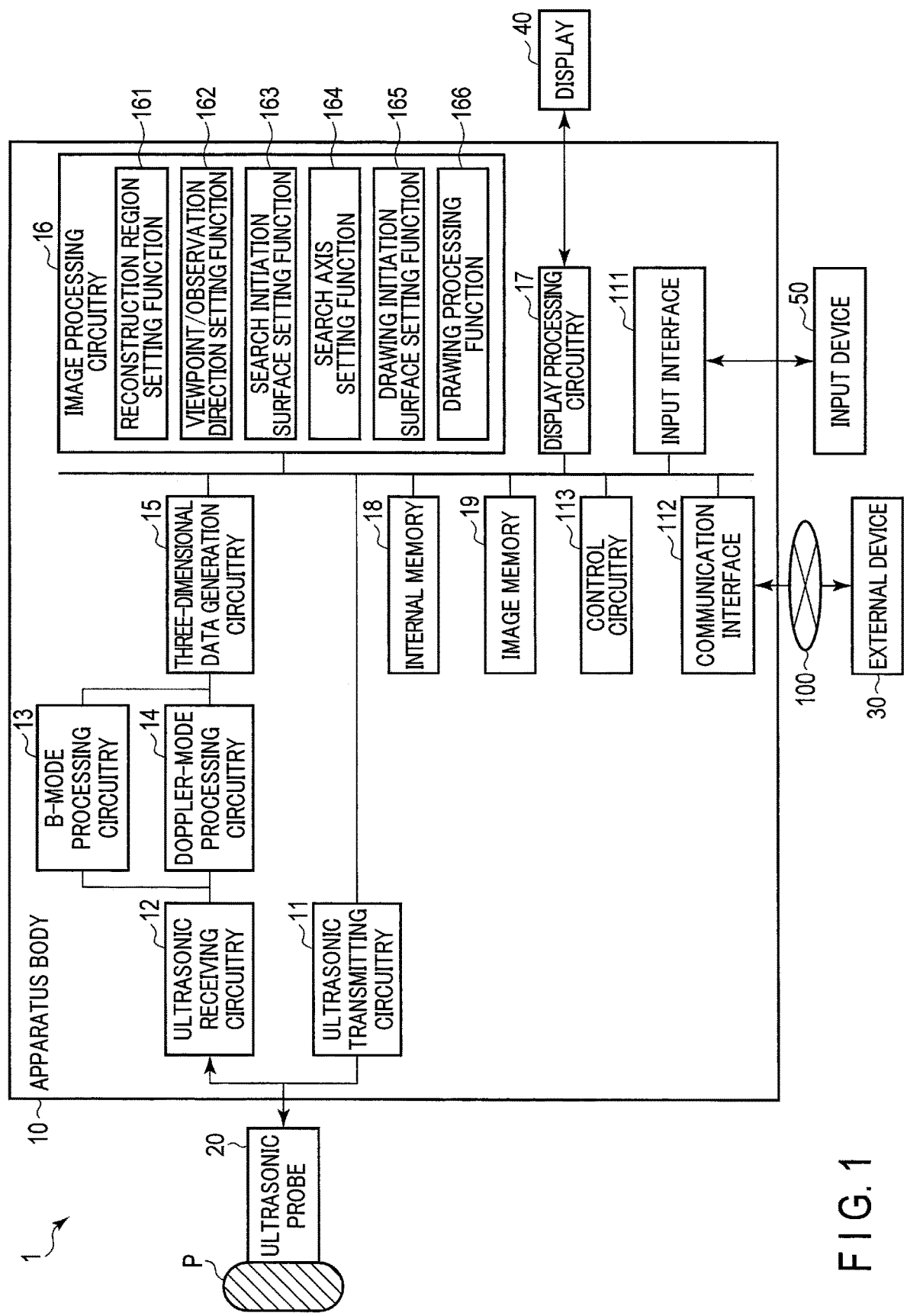
FIG. 1 is a block diagram showing the configuration of the medical image diagnostic apparatus according to the first embodiment.

In general, according to one embodiment, a medical image diagnostic apparatus includes processing circuitry. The processing circuitry sets a viewpoint and an observation direction relative to medical image data. The processing circuitry searches for a region that satisfies a predetermined requirement from a search initiation surface set at a predetermined position farther away from the viewpoint in comparison with a non-display region in the medical image data in a direction toward the viewpoint, and calculates a drawing initiation surface based on a result of the search. The processing circuitry executes drawing processing from the drawing initiation surface in the observation direction, and generates display image data.

Embodiments will be described below with reference to the drawings.

First Embodiment

FIG. 1 is a block diagram showing the configuration of the medical image diagnostic apparatus according to the first embodiment. An ultrasonic diagnostic apparatus 1 is described as an example of a medical image diagnostic apparatus, with reference to FIG. 1. As shown in FIG. 1, the ultrasonic diagnostic apparatus 1 includes an apparatus body 10 and an ultrasonic probe 20. The apparatus body 10 is connected to an external device 30 via a network 100. The apparatus body 10 is also connected to a display 40 and an input device 50.

The ultrasonic probe 20 includes a plurality of piezoelectric transducers, a matching layer provided to the piezoelectric transducers, and a backing material that prevents propagation of ultrasonic waves from the piezoelectric transducers to the rear side. The ultrasonic probe 20 is detachably connected to the apparatus body 10. The plurality of piezoelectric transducers generate ultrasonic waves based on a driving signal supplied from ultrasonic transmitting circuitry 11 provided in the apparatus body 10. The ultrasonic probe 20 may be provided with a button which is to be pressed in an offset process or in case of freezing of ultrasonic images.

Once the ultrasonic probe 20 transmits ultrasonic waves to a living body P, the transmitted ultrasonic waves are sequentially reflected by the boundary showing discontinuity of the acoustic impedance of the living tissue of the living body P, and are received as reflected wave signals by the plurality of piezoelectric transducers included in the ultrasonic probe 20. The amplitudes of the received reflected wave signals depend on the difference in the acoustic impedance at the boundary showing discontinuity of the acoustic impedance that affects the reflection of ultrasonic waves. If the transmitted ultrasonic pulses are reflected in a bloodstream or on the surface of the cardiac wall, the frequencies of the reflected wave signals are shifted depending on velocity components in the direction of transmitting ultrasonic waves in a moving object due to the Doppler effect. The ultrasonic probe 20 receives the reflected wave signals from the living body P, and converts the reflected wave signals into electrical signals.

In the present embodiment, the ultrasonic probe 20 is assumed to be, for example, a one-dimensional array probe in which a plurality of ultrasonic transducers are arranged along a predetermined direction. However, the ultrasonic probe 20 is not limited thereto, and may be a two-dimensional array probe in which piezoelectric transducers are arranged in a two-dimensional matrix form, or a mechanical four-dimensional probe in which piezoelectric transducers are mechanically swept in a direction orthogonal to the direction of transducer arrangement to realize a ultrasonic scan, etc, to the extent that the ultrasonic probe 20 is capable of acquiring volume data.

FIG. 1 merely illustrates a connection relationship between the ultrasonic probe 20 used for image capture and the apparatus body 10. However, the apparatus body 10 is capable of connecting a plurality of ultrasonic probes. The connected plurality of ultrasonic probes can be switched discretionarily to be selected for use in image capture.

The apparatus body 10 shown in FIG. 1 is an apparatus that generates an ultrasonic image, based on reflected wave signals received by the ultrasonic probe 20. As shown in FIG. 1, the apparatus body 10 includes ultrasonic transmitting circuitry 11, ultrasonic receiving circuitry 12, B-mode processing circuitry 13, Doppler-mode processing circuitry 14, three-dimensional data generation circuitry 15, image processing circuitry 16, display processing circuitry 17, internal memory 18, an image memory 19 (cine memory), an input interface 111, a communication interface 112, and control circuitry 113.

The ultrasonic transmitting circuitry 11 is a processor that supplies a driving signal to the ultrasonic probe 20. The ultrasonic transmitting circuitry 11 is implemented, for example, by trigger-generation circuitry, delay circuitry, pulser circuitry, etc. The trigger-generating circuitry repeatedly generates rate pulses for forming transmission ultrasonic waves at a predetermined rate frequency. The delay circuitry converges ultrasonic waves generated from the ultrasonic probe 20 as a beam, and applies, to each rate pulse generated by the trigger generation circuitry, a transmission delay time for each piezoelectric transducer required for determining a transmission directivity. The pulser circuitry supplies driving signals (driving pulses) to the plurality of ultrasonic transducers provided in the ultrasonic probe 20 at a timing based on the rate pulse. By changing the delay time to be applied to each rate pulse from the delay circuitry, the transmission direction from the piezoelectric transducer surface can be discretionarily adjusted.

The ultrasonic receiving circuitry 12 is a processor that executes various processes on reflected wave signals received by the ultrasonic probe 20 to generate a receive signal. The ultrasonic receiving circuitry 12 is implemented, for example, by amplification circuitry, an A/D converter, reception delay circuitry, and an adder, etc. The amplification circuitry executes a gain correction process for each channel by amplifying reflected wave signals received by the ultrasonic probe 20. The A/D converter converts the gain-corrected reflected wave signals into digital signals. The reception delay circuitry delays input of the digital signals to the adder by a delay time required for determining a reception directivity. The adder adds a plurality of digital signals in which the delay time has been applied. After the addition processing of the adder, receive signals are generated in which a reflected component from the direction corresponding to the receive directivity is emphasized.

The B-mode processing circuitry 13 is a processor that generates B-mode data, based on the receive signals received from the ultrasonic receiving circuitry 12. The B-mode processing circuitry 13 executes an envelope detection process and a logarithmic amplification process, etc. on the receive signals received from the ultrasonic receiving circuitry 12, and generates data (B-mode data) in which the signal intensity is expressed by the brightness intensity. The generated B-mode data is stored in a non-illustrated RAW data memory as B-mode RAW data on a two-dimensional ultrasonic scanning line.

The Doppler-mode processing circuitry 14 is a processor that generates a Doppler waveform and Doppler data, based on the receive signals received from the ultrasonic receiving circuitry 12. The Doppler-mode processing circuitry 14 extracts a blood flow signal from the receive signal, generates a Doppler waveform from the extracted blood flow signal, and generates data (Doppler data) in which information, such as a mean velocity, dispersion, power, etc. is extracted from the blood flow signal with respect to multiple points. The generated Doppler data is stored in the non-illustrated RAW data memory as Doppler RAW data on a two-dimensional ultrasonic scanning line.

The three-dimensional data generation circuitry 15 is a processor that generates three-dimensional image data based on data generated by the B-mode processing circuitry 13 and the Doppler-mode processing circuitry 14. The three-dimensional data generation circuitry 15, for example, executes RAW-pixel conversion relative to B-mode RAW data stored in a RAW data memory to generate two-dimensional image data consisting of pixels.

In addition, the three-dimensional data generation circuitry 15 executes, to B-mode RAW data stored in the RAW data memory, RAW-voxel conversion which includes an interpolation process taking spatial position information into consideration to generate three-dimensional image data (hereinafter referred to as volume data) consisting of voxels in a desired range.

The image processing circuitry 16 is a processor that executes predetermined image processing to the two-dimensional image data or the volume data. The predetermined image processing includes, for example, volume rendering, surface rendering, multi-planar reconstruction (MPR), and maximum intensity projection (MIP), etc. The image processing circuitry 16 inserts a two-dimensional filter after the image processing to perform spatial smoothing in order to reduce noises or to improve image continuity.

The image processing circuitry 16 executes rendering processing after a region which obstructs an observation target region, and is unnecessary for observation, is deleted. Specifically, the image processing circuitry 16, for example, executes an image processing program stored in the internal memory 18 to accomplish a function corresponding to the program. The image processing circuitry 16, for example, has a reconstruction region setting function 161, a viewpoint/observation direction setting function 162, a search initiation surface setting function 163, a search axis setting function 164, a drawing initiation surface setting function 165, and a drawing processing function 166.

The reconstruction region setting function 161 is a function of setting a reconstruction region. In the present embodiment, for example, the reconstruction region is a region to be targeted for processing to convert generated volume data into a two-dimensional image which is three-dimensionally or four-dimensionally observable. Specifically, for example, via the reconstruction region setting function 161, the image processing circuitry 16 receives, from an operator, a designation of an ROI region relative to a tomographic image generated based on the two-dimensional image data and displayed on the display 40. The image processing circuitry 16 sets a reconstruction region as a three-dimensional region based on the designated ROI region.

The image processing circuitry 16, for example, may automatically set a three-dimensional region that includes a region extracted using the known region extraction algorithm, such as pattern recognition, etc. as the reconstruction region. The image processing circuitry 16 may set the entire volume data as the reconstruction region, instead of part of volume data.

The viewpoint/observation direction setting function 162 is a function of setting a viewpoint that represents a position where a three-dimensional image or a four-dimensional image is observed, and an observation direction represents the direction toward which an image is observed. Specifically, for example, via the viewpoint/observation direction setting function 162, the image processing circuitry 16 receives a designation of the viewpoint and the observation direction when observing a three-dimensional image or a four-dimensional image. The image processing circuitry 16 sets the designated viewpoint and observation direction. In the present embodiment, the forward direction of the observation direction is the direction starting from the viewpoint.

The viewpoint and the observation direction may be set, for example, by a procedure similar to the known procedure for converting volume data into a two-dimensional image which is three-dimensionally or four-dimensionally observable.

The search initiation surface setting function 163 is a function of setting a search initiation surface as a set of voxels from which a search for the reconstruction region is initiated. The search initiation surface is used for searching for a boundary between regions which have different physical properties within the reconstruction region from an opposite side of the viewpoint. Specifically, for example, via the search initiation surface setting function 163, the image processing circuitry 16 sets the search initiation surface at a position passing through an observation target region which is farther away from the set viewpoint than a region to be deleted.

The search axis setting function 164 is a function of setting a search axis which represents a search direction for searching for a boundary in the reconstruction region from voxels on the search initiation surface. Specifically, for example, via the search axis setting function 164, the image processing circuitry 16 sets the search axis based on the observation direction, the search initiation surface, etc. In the present embodiment, the forward direction of the search axis is the direction toward the viewpoint.

The drawing initiation surface setting function 165 is a function of calculating a drawing initiation surface as a set of voxels from which rendering processing is initiated in volume data. Specifically, for example, via the drawing initiation surface setting function 165, the image processing circuitry 16 calculates the drawing initiation surface based on results of a search from the search initiation surface.

The drawing processing function 166 is a function of generating rendering image data in which volume data is projected onto a two-dimensional image. Specifically, for example, via the drawing processing function 166, the image processing circuitry 16 executes the rendering processing of volume data toward the observation direction from the drawing initiation surface, and generates rendering image data as display image data.

The display processing circuitry 17 shown in FIG. 1 is a processor that converts various types of image data generated or processed at the image processing circuitry 16 into a video signal. Specifically, the display processing circuitry 17 executes various types of processing such as dynamic range, brightness, contrast and y curve corrections, and RGB conversion, etc., to various types of image data generated or processed at the image processing circuitry 16, in order to convert the image data to a video signal. The display processing circuitry 17 directs the display 40 to display the video signal. The display processing circuitry 17 may generate a user interface (GUI: Graphical User Interface) through which an operator inputs various instructions by the input interface 111, and directs the display 40 to display the GUI. The display 40 may adopt, for example, a CRT display, a liquid crystal display, an organic EL display, an LED display, a plasma display, or any other display known in this technical field.

The internal memory 18 includes, for example, a storage medium which is readable by a processor, such as a magnetic or optical storage medium, or a semiconductor memory, etc. The internal memory 18 stores a program for implementing ultrasonic transmission/reception, a program for executing image processing, a program for executing display processing, a program for controlling sensitivity of the ultrasonic probe 20, etc. In addition, the internal memory 18 stores diagnosis information (e.g., patient ID, doctor's findings, etc.), a diagnosis protocol, transmission conditions, receiving conditions, signal processing conditions, image generation conditions, image processing conditions, a body mark generation program, display conditions, and data such as a conversion table for presetting a range of color data for use in imaging, with respect to each of regions of diagnosis. The above programs and data may be stored in the internal memory 18. For example, the programs and data may be distributed as being stored in a non-volatile storage medium, and the programs and data may be read from the non-volatile storage medium and installed into the internal memory 18.

In addition, the internal memory 18 stores two-dimensional image data and volume data generated by the three-dimensional data generation circuitry 15, and image data generated and processed by the image processing circuitry 16, in accordance with a storing operation input through the input interface 111. The internal memory 18 can transfer the stored data to the external device 30 via the communication interface 112.

The internal memory 18 may be a drive, etc. which reads and writes various types of information relative to a portable storage medium, such as a CD-ROM drive, a DVD drive, and a flash memory. The internal memory 18 can write the stored data into a portable storage medium, and store the data in the external device 30 via the portable storage medium.

The image memory 19 includes, for example, a storage medium which is readable by a processor, such as a magnetic or optical storage medium, or a semiconductor memory. The image memory 19 stores image data corresponding to a plurality of frames immediately before a freeze operation input through the input interface 111. The image data stored in the image memory 19 is successively displayed (cine-displayed), for example.

The internal memory 18 and the image memory 19 are not necessarily to be implemented by separate storage devices. The internal memory 18 and the image memory 19 may be implemented by a single storage devices. The internal memory 18 and the image memory 19 may be implemented respectively by a plurality of storage devices.

The input interface 111 receives various types of instructions from an operator through the input device 50. The input device 50 is, for example, a mouse, a keyboard, a panel switch, a slider switch, a trackball, a rotary encoder, an operation panel, or a touch command screen (TCS). The input interface 111 is connected to the control circuitry 113, for example, via a bus. The input interface 111 converts an operation instruction input by the operator into electric signals, and outputs the electric signals to the control circuitry 113. In the present embodiments, the input interface 111 is not limited to be connected to physical operation components such as a mouse, a keyboard, etc. For example, the input interface 111 may include processing circuitry which receives an electric signal corresponding to an operation instruction input from an external input device independently provided from the ultrasonic diagnostic apparatus 1, and outputs the electric signal to the control circuitry 113.

The communication interface 112 is connected to the external device 30 via the network 100, etc., and performs data communication with the external device 30. The external device 30 is, for example, a database such as a PACS (Picture Archiving and Communication System) which is a system for managing various medical image data, an electronic medical record system for managing electronic medical records to which medical images are added, etc. In addition, the external device 30 may, for example, be any medical image diagnostic apparatus other than the ultrasonic diagnostic apparatus 1 according to the present embodiment, such as an X-ray CT (Computed Tomography) apparatus, an MRI (Magnetic Resonance Imaging) apparatus, a nuclear medical diagnostic apparatus, an X-ray diagnostic apparatus, etc. Any standards may be applied for communication with the external device 30. For example, DICOM (digital imaging and communication in medicine) may be applied.

The control circuitry 113 is a processor acting as a nerve center of the ultrasonic diagnostic apparatus 1, for example. The control circuitry 113 executes a control program stored in the internal memory 18 to realize a function corresponding to the program.

Next to be described is the operation of the ultrasonic diagnostic apparatus 1 having the aforementioned configuration when generating a two-dimensional image by which an observation target can be three-dimensionally or four-dimensionally observed. An example where the observation target is a fetus will be described below.

For example, it is assumed that an operator performs ultrasonic inspection on a pregnant woman carrying a fetus by using the ultrasonic probe 20. Ultrasonic waves transmitted from the ultrasonic probe 20 to the pregnant woman are sequentially reflected by the boundary showing discontinuity of the acoustic impedance of the living tissue of the pregnant woman, and are received as reflected wave signals by the ultrasonic probe 20. The ultrasonic receiving circuitry 12 executes various types of processes on the reflected wave signals received by the ultrasonic probe 20 to generate a receive signal.

The B-mode processing circuitry 13 generates B-mode RAW data on the two-dimensional ultrasonic scanning line, based on the receive signal received from the ultrasonic receiving circuitry 12. The three-dimensional data generation circuitry 15 executes RAW-pixel conversion relative to the two-dimensional B-mode RAW data generated by the B-mode processing circuitry 13 to generate two-dimensional image data. The generated two-dimensional image data is subjected to image processing by the image processing circuitry 16 and conversion processing by the display processing circuitry 17, and is displayed on the display 40 as a tomographic image.

The operator, for example, operates the ultrasonic probe 20 so that a face of a fetus is included in the tomographic image displayed on the display 40 if the face of the fetus is intended to be observed. If the tomographic image that includes a desired region is displayed, the operator inputs via the input interface 111 an instruction to execute a four-dimensional image display in which regions unnecessary for observation, such as arms and an umbilical cord of the fetus, placentas, etc. are deleted. If the instruction is input, the image processing circuitry 16 reads, from the internal memory 18, an image processing program to execute rendering processing after a region unnecessary for observation which obstructs an observation target region is deleted, and executes the read program.

Figure 2:
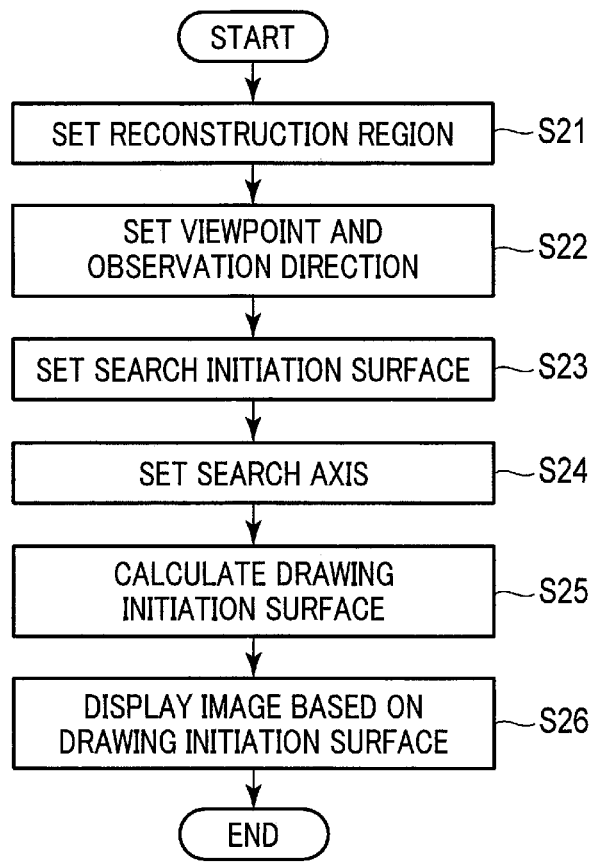
FIG. 2 is a flowchart of the operation when generating rendering image data by image processing circuitry shown in FIG. 1.

FIG. 2 is a flowchart of an example of the operation of the image processing circuitry 16 shown in FIG. 1 when generating rendering image data in which a region unnecessary for observation, and which obstructs an observation target region, has been deleted.

If the image processing program is executed, for example, the reconstruction region setting function 161 is first accomplished. Via the reconstruction region setting function 161, the image processing circuitry 16 receives from the operator via the input interface 111 a designation of an ROI region relative to a tomographic image displayed on the display 40.

Figure 3:
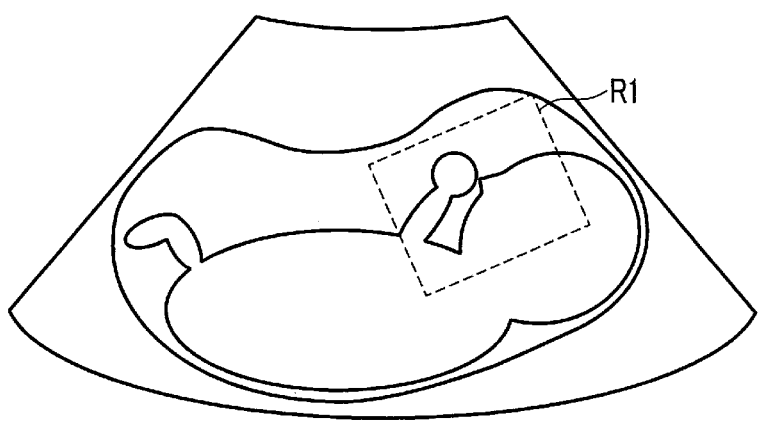
FIG. 3 is a diagram showing an ROI region designated relative to a tomographic image displayed on a display shown in FIG. 1.

FIG. 3 is a diagram showing an ROI region R1 designated relative to the tomographic image displayed on the display 40. In FIG. 3, a rectangle ROI region R1 is designated in a region that includes the face of the fetus. The image processing circuitry 16 sets a reconstruction region in the volume data, based on the designated ROI region R1 (Step S21). The ROI region may be expressed by a curve manually drawn by the operator on the tomographic image.

The image processing circuitry 16, for example, may automatically set a three-dimensional region that includes a face region extracted using the known region extraction algorithm such as pattern recognition, etc. as the reconstruction region.

Once the reconstruction region is set, the image processing circuitry 16 executes the viewpoint/observation direction setting function 162. After executing the viewpoint/observation direction setting function 162, the image processing circuitry 16 sets a viewpoint and an observation direction for observing a three-dimensional image or a four-dimensional image, in a procedure similar to that executed in the known rendering processing (step S22). For example, the image processing circuitry 16 sets a viewpoint and an observation direction based on the designation of coordinates of the viewpoint and the observation direction input by the operator via the input interface 111. In this case, the image processing circuitry 16 takes direction farther away from the viewpoint to be the forward direction and sets the direction as the observation direction. The image processing circuitry 16 may automatically set the observation direction as the direction identical to the direction in which the ultrasound beams are applied.

Once the viewpoint and the observation direction are set, the image processing circuitry 16 executes the search initiation surface setting function 163. After executing the search initiation surface setting function 163, the image processing circuitry 16 sets a search initiation surface at a position farther away from a non-display region such as arms, an umbilical cord, and placentas, etc., from the set viewpoint (step S23). In this case, the search initiation surface may pass through part of the fetal region which is to be displayed.

Specifically, the image processing circuitry 16 sets, for example, part of a surface constituting the reconstruction region as the search initiation surface. FIG. 4 is a diagram showing an example of a search initiation surface S1 set by using part of surfaces constituting a reconstruction region. In FIG. 4, a cross-section corresponding to a side farthest away from the viewpoint among four sides of the ROI region R1 corresponding to the reconstruction region is set to the search initiation surface S1. If the ROI region R1 is expressed by a manually input curve, the image processing circuitry 16 may set the search initiation surface S1 by using part of the curved surfaces constituting the reconstruction region set by the ROI region R1.

The search initiation surface is not limited to be set by using part of the surfaces constituting the reconstruction region. The image processing circuitry 16, for example, may set the search initiation surface based on a predetermined structure within the living body. For example, the image processing circuitry 16 executes the known region extraction algorithm such as pattern recognition, etc. relative to the tomographic image, and extracts a region representing the head of the fetus, as the structure within the living body. The image processing circuitry 16 may set a cross-section corresponding to a line passing through a point within the extracted head region as the search initiation surface.

Specifically, the image processing circuitry 16 may set a cross-section corresponding to a line passing through a point within the head region of the fetus and orthogonal to the observation direction as the search initiation surface. FIG. 5 is a diagram showing an example of a search initiation surface S1 set by using a line passing through a point P1 in the head region and orthogonal to the observation direction. In FIG. 5, for example, the head region of the fetus is extracted in the ROI region R1 designated to include the entire head region of the fetus, and the search initiation surface S1 is set by using the point P1 within the extracted head region.

The image processing circuitry 16, for example, may set a plurality of search initiation surfaces. For example, when volume data is projected to a two-dimensional image, if the observation direction does not pass through the search initiation surface, a surface farther away from the viewpoint among the surfaces constituting the reconstruction region may be added as a search initiation surface.

The image processing circuitry 16, for example, may set a search initiation surfaces of a certain time phase, by using a search initiation surface set in a different time phase. For example, the image processing circuitry 16 may set, as a search initiation surface of the next time phase, a set of voxels obtained by approximating each voxel on the search initiation surface set in the previous time phase to each voxel of a drawing initiation surface calculated in the current time phase, along the search axis direction.

Figure 6:
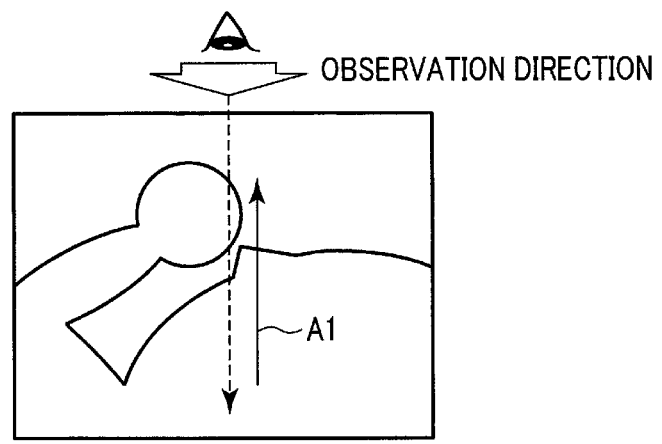
FIG. 6 is a diagram showing a search axis set to be parallel to an observation direction, in which the direction toward a viewpoint is a forward direction.

Once the search initiation surface is set, the image processing circuitry 16 executes the search axis setting function 164. After executing the search axis setting function 164, the image processing circuitry 16 sets a search axis (step S24). Specifically, the image processing circuitry 16, for example, sets the search axis which is parallel to the observation direction, and in which the direction toward the viewpoint is the forward direction. FIG. 6 is a diagram showing an example of a search axis A1 set to be parallel to the observation direction, in which the direction toward the viewpoint is the forward direction.

The search axis need not be parallel to the observation direction. For example, the image processing circuitry 16 may set the search axis in the direction of the normal to the search initiation surface.

Figure 7:
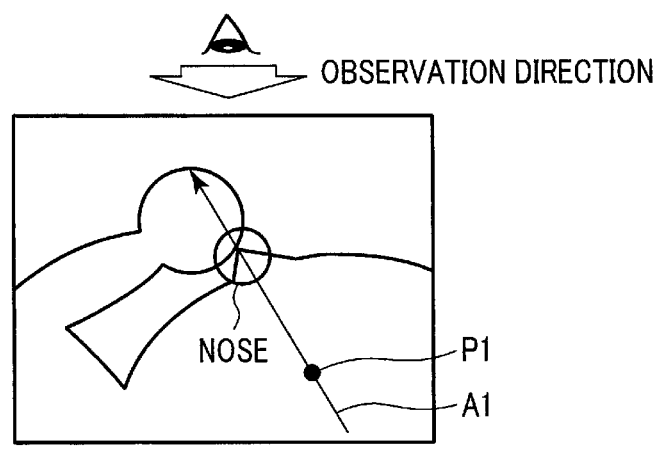
FIG. 7 is a diagram showing a search axis set to pass through a point of a head toward a nose of a fetus, in which the direction toward a viewpoint is a forward direction.

In addition, the image processing circuitry 16 may set the search axis in the frontal direction from the observation target. The frontal direction may be the frontal direction of a face detected by the known facial recognition algorithm, etc., for example. Specifically, the image processing circuitry 16, for example, automatically sets a direction from a point within the head region of the fetus toward the nose as the search axis. FIG. 7 is a diagram showing an example of the search axis A1 set to be the direction passing through a point P1 of the head region of the fetus toward the nose, in which the direction toward the viewpoint is the forward direction.

Figure 8:
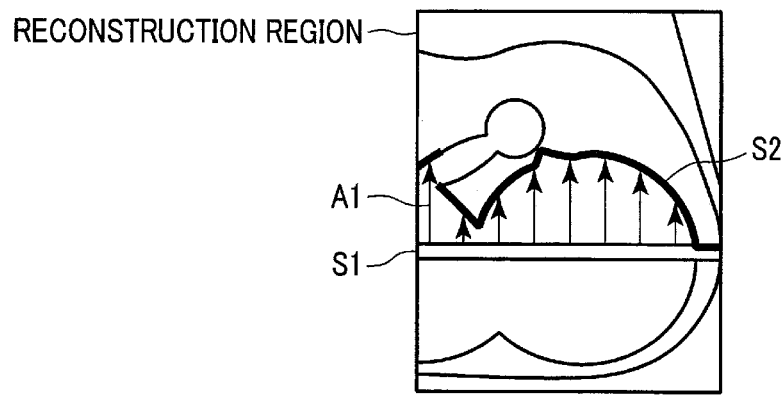
FIG. 8 is a diagram showing a drawing initiation surface obtained by a search along the search axis A1 from the search initiation surface.

Once the search axis is set, the image processing circuitry 16 executes the drawing initiation surface setting function 165. After executing the drawing initiation surface setting function 165, the image processing circuitry 16 calculates a drawing initiation surface based on the boundary between a fetal region and an amniotic fluid region obtained by a search along the search axis from the search initiation surface (Step S25). FIG. 8 is a diagram showing an example of a drawing initiation surface S2 calculated based on the boundary surface obtained by a search along the search axis A1 from the search initiation surface S1.

Figure 9:
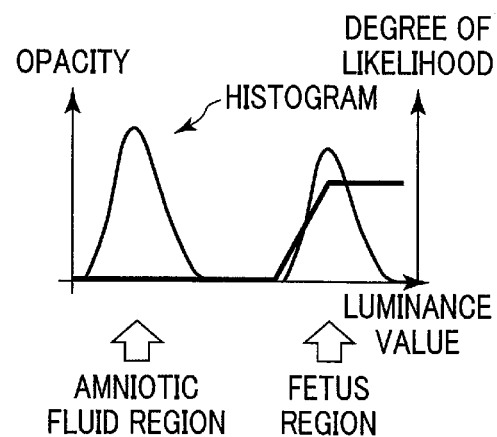
FIG. 9 is a drawing showing an opacity curve in which a fetal region is a display region, and an amniotic fluid region is a non-display region.
Figure 10:
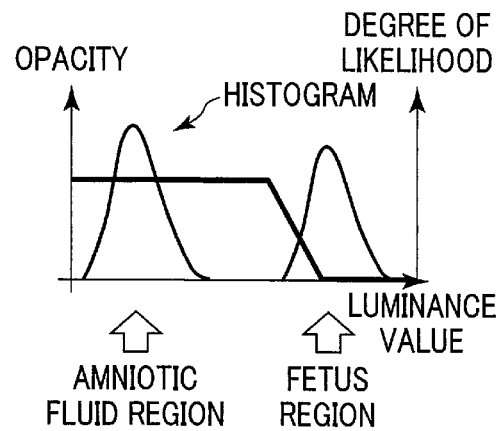
FIG. 10 is a drawing showing an opacity curve obtained by reversing the opacity curve shown in FIG. 9.

The image processing circuitry 16, for example, calculates a drawing initiation surface by the processing below. For example, the image processing circuitry 16 stores an opacity curve with reversed opacity, in which the opacity of the opacity curve representing that the fetal region is a display region, and the amniotic fluid region is a non-display region is reversed. FIG. 9 is a drawing showing an example of an opacity curve in which the fetal region is set as a display region, namely, the opacity is set to be high, and the amniotic fluid region is set as a non-display region, namely, the opacity is set to be low. The opacity curve shown in FIG. 9 is set to increase the opacity with a predetermined contrast from the luminance values for which the fetal region likely has, based on a histogram indicating the degree of likelihood of the fetal region relative to the luminance of a voxel. On the other hand, FIG. 10 is a drawing showing an example of an opacity curve in which the opacity curve of FIG. 9 is reversed. Namely, in FIG. 10, the opacity is low in the fetal region, and the opacity is high in the amniotic fluid region. The image processing circuitry 16 uses the opacity curve shown in FIG. 10, and calculates as the drawing initiation surface a set of voxels in which the transmission coefficient of ray becomes zero when ray casting is performed along the search axis from the search initiation surface.

The method of calculating the drawing initiation surface is not limited to the above method. The image processing circuitry 16 may acquire a boundary between the fetal region and the amniotic fluid region, or a region close to the boundary, by using any known algorithm, and calculate the drawing initiation surface based on the acquired boundary or region close to the boundary. Specifically, the image processing circuitry 16, for example, sets the observation target to be a display region, and a non-observation target to be a non-display region. The image processing circuitry 16 calculates, as the drawing initiation surface, a set of first voxels when a search along the search axis from the search initiation surface has reached a non-display region.

The image processing circuitry 16 may calculate as the drawing initiation surface a set of first voxels which have the voxel value exceeding or falling below a threshold value that the search along the search axis from the search initiation surface has reached, the threshold value being a value between a luminance value (voxel value) indicating a fetal region and a luminance value indicating an amniotic fluid region.

When searching for a boundary between these regions along the search axis, a change in voxel value in the volume data must be greater in a region changing from the fetal region to the amniotic fluid region. The image processing circuitry 16 may calculate a set of voxels in which the change in voxel value exceeds a predetermined threshold value as the drawing initiation surface.

In step S23, when a plurality of search initiation surfaces are set, the image processing circuitry 16 initiates a search of the boundary region from voxels on a search initiation surface closest to the set viewpoint. FIG. 11 is a diagram showing an example of a drawing initiation surface S2 calculated in a case where multiple search initiation surfaces are set. In FIG. 11, search initiation surfaces S1-1 and S1-2 are set, a viewpoint is set at a right upper region of FIG. 11, and a search axis is set to be parallel to the observation direction. In this case, a search is initiated from voxels on a region indicated by a bold solid line close to the viewpoint on the search initiation surface S1-1, and a search is initiated from voxels on a region indicated by a bold solid line close to the viewpoint on the search initiation surface S1-2. In FIG. 11, a search initiation surface is set to be a surface farther away from the viewpoint among surfaces constituting the reconstruction region, relative to regions in which lines of sight in the observation direction do not cross a search initiation surface other than the search initiation surfaces S1-1 and S1-2.

If the image processing circuitry 16 executes surface rendering, the image processing circuitry 16 may set the drawing initiation surface to be a polygon closest to the search initiation surface, when searching in the forward direction of the search axis along the search axis from each voxel of the search initiation surface.

In calculation of the drawing initiation surface, the volume data used for the calculation may be the volume data generated in the three-dimensional data generation circuitry 15, or the volume data subjected to image processing such as smoothing, differential filter (edge extraction), and expansion processing, etc. by the image processing circuitry 16. There is a case where an ultrasonic signal of an amniotic fluid and an ultrasonic signal of a brain tissue of a fetus are difficult to distinguish in ultrasonic images. By using volume data subjected to image processing such as smoothing, differential filter, and expansion processing, etc., there may be a case where the amniotic fluid and the brain tissue of the fetus can be easily distinguished.

The image processing circuitry 16 is not necessary for calculating the drawing initiation surface. For example, the image processing circuitry 16 may use a drawing initiation surface calculated in the previous time phase in the current time phase. The time phase in which the drawing initiation surface may either be discretionarily determined or recalculated in a predetermined cycle.

In the above example, when calculating a drawing initiation surface, the boundary between the fetal region and the amniotic fluid region or a region close to the boundary is acquired. However, the target may not be limited to the amniotic fluid. For example, the image processing circuitry 16 sets a region of voxel values indicating the fetal region. The image processing circuitry 16 searches for voxels having a voxel value outside the set range along the search axis from the search initiation surface. Then, the image processing circuitry 16 may calculate a set of first voxels having the voxel values outside the set range that the search has reached as a drawing initiation surface. In this case, the voxels calculated as the drawing initiation surface need not be a boundary between the fetal region and the amniotic fluid region, but may be a boundary between the fetal region and a region other than the fetal region.

In the calculation of the drawing initiation surface, the method using a form of processing which does not lose the real time property when displaying the volume data as a four-dimensional image has been described. However, if the operator does not focus on the real time property or if the known region extraction algorithm does not lose the real time property, it may be possible to calculate, as a drawing initiation surface, first points that the search along the search axis from the search initiation surface has reached after the amniotic fluid region is extracted by the known region extraction algorithm. In this case, the image processing circuitry 16 may set any continuous regions extracted by using the known region extraction algorithm as non-display regions.

Once the drawing initiation surface is calculated, the image processing circuitry 16 executes the drawing processing function 166. After executing the drawing processing function 166, the image processing circuitry 16 executes rendering processing on the volume data along the observation direction from the drawing initiation surface to generate rendering image data (step S26).

Specifically, the image processing circuitry 16 uses, for example, the general opacity curve shown in FIG. 9, in which the fetal region is set as a display region, and the amniotic fluid region is set as a non-display region, and executes rendering on the volume data along the observation direction from the drawing initiation surface to generate rendering image data of the fetal region which is an observation target. FIG. 12 is a drawing showing an example of rendering processing on the volume data executed along an observation direction from the drawing initiation surface. Via this processing, for example, rendering image data in which a face region of a fetus is set as a display region, and an arm region is set as a non-display region is generated, as shown in FIG. 13.

The opacity curve used in this rendering processing may be different from the opacity curve shown in FIG. 9. For example, the opacity curve used when calculating the drawing initiation surface may have the lower contrast than the opacity curve used for the rendering processing. When calculating the drawing initiation surface via using the opacity curve having the low contrast, it is possible to avoid setting the drawing initiation surface within the fetal region, and to facilitate the setting of the drawing initiation surface within the amniotic fluid region.

The rendering image data generated by the image processing circuitry 16 is converted to video signals by the display processing circuitry 17, and displayed on the display 40. Via this processing, it is possible to display the face of the fetus on the display 40 as a two-dimensional image which can be three-dimensionally or four-dimensionally observed, while deleting an unnecessary region such as an arm, etc., for example, as shown in FIG. 14.

The operator may change the position of the search initiation surface set in step S23 and the setting method, if required, after confirming the image displayed on the display 40. For example, if a region that the operator intended to display is not displayed in the image displayed on the display 40, due to the application of the processing according to the present embodiment, the operator may manually change the position of the search initiation surface and the setting method.

In addition, the operator may change the setting method of the search axis set in step S24, if required, after confirming the image displayed on the display 40. For example, if a region that the operator intended to display is not displayed in the image displayed on the display 40, due to the application of the processing according to the present embodiment, the operator may manually change the setting method of the search axis.

The processing of the image processing circuitry 16 in the drawing processing function 166 is not limited to the aforementioned processing. For example, the image processing circuitry 16 may display a region corresponding to the search initiation surface generated in step S23 on the two-dimensional image by which the face of the fetus can be three-dimensionally or four-dimensionally observed. In addition, the image processing circuitry 16 may display a region corresponding to the drawing initiation surface calculated in step S25 on this two-dimensional image.

Furthermore, the image processing circuitry 16 may display, for example, a tomographic image which distinguishably shows a region displayed by rendering, in addition to the two-dimensional image by which the face of the fetus can be three-dimensionally or four-dimensionally observed. For example, the image processing circuitry 16 may display the tomographic image in which a surface of a region which is four-dimensionally displayed is colored to be distinguished from a non-display region. FIG. 15 is a drawing showing an example of a tomographic image in which a surface of a display region is colored to be distinguished from a non-display region. In FIG. 15, the surface of the fetal region except the arm region is indicated by a red bold line, for example, as a region which is four-dimensionally displayed on the tomographic image.

The image processing circuitry 16 may display a tomographic image in which a range of a region which is four-dimensionally displayed is colored to be distinguished from a non-display region. FIG. 16 is a drawing showing an example of a tomographic image in which a range of a display region is colored to be distinguished from a non-display region. In FIG. 16, the range of the fetal region except the arm region is colored by red, for example, as a region which is four-dimensionally displayed on the tomographic image.

The image displayed on the display 40 is not limited to a rendering image obtained by the processing according to the present embodiment. For example, the image processing circuitry 16 may display a fetus based on the first rendering image obtained by the processing according to the present embodiment and the second rendering image obtained by the general rendering processing. In the present embodiment, the general rendering processing is rendering processing which is executed from the viewpoint set in step S22 toward the observation direction set in step S22. Specifically, the image processing circuitry 16 acquires a differential image between the first rendering image and the second rendering image. The image processing circuitry 16 may superimpose the obtained differential image in which the transparency, color, or both of them have been changed with the first rendering image, and display the combined image. Via this processing, as shown in FIG. 17, for example, the region such as the arm region which is set to be a non-displayed region in the present embodiment is translucently superimposed on the first rendering image.

Via the drawing processing function 166, the image processing circuitry 16 is not necessary to execute rendering processing on the volume data along the observation direction from the drawing initiation surface. For example, if the rendering image by surface rendering is displayed on the display 40, the image processing circuitry 16 may set the polygon indicating the drawing initiation surface calculated in step S25 as a display target.

As described above, according to the first embodiment, the image processing circuitry 16 sets the viewpoint and the observation direction relative to the ultrasonic image data such as volume data. The image processing circuitry 16 sets a search initiation surface at a predetermined position farther away from the set viewpoint in comparison with the non-display region in the ultrasonic image data. The image processing circuitry 16 searches for a region which satisfies a predetermined requirement toward the viewpoint from the set search initiation surface, and calculates a drawing initiation surface based on the search results. The image processing circuitry 16 then executes drawing processing from the calculated drawing initiation surface toward the observation direction to generate display image data.

Via this processing, it is possible to efficiently set a drawing initiation surface which is a surface from which the rendering processing is initiated between the face of the fetus, which is the observation target, and an object unnecessary for observation, such as an arm, an umbilical cord, and placentas, etc. Thus, even if an arm, an umbilical cord, etc. unnecessary for observation is located in front of the face of the fetus, the face of the fetus which is the observation target can be displayed in high speed. In this method, there is no need to execute a slow process such as region extraction, etc. under four-dimensional image display. Accordingly, the method demonstrates excellent real time properties. In addition, since rendering is initiated from a region close to the fetus surface, it is possible to reduce the influence of body wastes in the amniotic fluid or noises. Furthermore, it is possible to use the CPU for other slow processes, meaning that the CPU can be efficiently used.

It has been described that setting of the reconstruction region, setting of the search initiation surface, and calculation of the drawing initiation surface are performed by using the region extraction processing such as pattern recognition, etc.; however, these processes are merely needed to be executed once at the time of commencing the method, and accordingly, the real time property is not degraded.

In the first embodiment, the image processing circuitry 16 executes the known region extraction algorithm such as pattern recognition, etc. on the tomographic image, and a region expressing a predetermined structure in the living body is extracted. The image processing circuitry 16 sets a cross-section corresponding to a line passing through a point within the extracted region as the search initiation surface. Via this processing, the search initiation surface is automatically set.

In the first embodiment, the image processing circuitry 16 sets the reconstruction region in the ultrasonic image data and sets the search initiation surface within the reconstruction region. Via this processing, the load of the search for the drawing initiation surface and the rendering processing from the drawing initiation surface can be reduced.

In the first embodiment, the image processing circuitry 16 sets a search initiation surface at a position farther away from the viewpoint in comparison with the region unnecessary for observation in the ultrasonic image data, but not outside the boundary of the reconstruction region farther away from the viewpoint. Accordingly, the range where the search initiation surface can be set may be broader between the surface of the region unnecessary for observation and the boundary of the observation target (farther away from the viewpoint).

In the first embodiment, the image processing circuitry 16 may set a plurality of search initiation surfaces. In this case, the image processing circuitry 16 initiates a search for a region that satisfies a predetermined requirement from the search initiation surface closer to the set viewpoint. Via this process, it is possible to discretionarily narrow the display regions.

In the first embodiment, the image processing circuitry 16 may set a search initiation surface of the current time phase by using the search initiation surface set in a different time phase. Via this process, it is possible to reduce the time required for setting the search initiation surface.

In the first embodiment, the image processing circuitry 16 may use the drawing initiation surface calculated in a different time phase as the drawing initiation surface in the current time phase. Via this process, it is possible to reduce the time required for setting the drawing initiation surface.

In the first embodiment, the image processing circuitry 16 calculates the drawing initiation surface by using the first opacity curve in which the opacity of the display region is set to be low, and the opacity of the non-display region is set to be high, with a predetermined contrast. The image processing circuitry 16 may execute drawing processing by using the second opacity curve in which the opacity of the display region is set to be high, and the opacity of the non-display region is set to be low with a contrast higher than the first opacity curve. Via this process, it is possible to prevent the drawing initiation surface from being set within the display region, and to facilitate the drawing initiation surface being set within the non-display region.

In the first embodiment, the image processing circuitry 16 may superimpose a region corresponding to the search initiation surface with the display image data generated by the drawing processing. Via this process, the operator can confirm the search initiation surface used for generating a fourth-dimensional image when observing the fourth-dimensional image.

In the first embodiment, the image processing circuitry 16 may superimpose a region corresponding to the drawing initiation surface with the display image data generated by the drawing processing. Via this process, the operator can confirm the drawing initiation surface used for generating a fourth-dimensional image when observing the fourth-dimensional image.

In the first embodiment, the image processing circuitry 16 may superimpose the display image data generated by the drawing processing with a differential image between the display image data and display image data generated by executing the drawing processing toward the observation direction from the viewpoint. Via this process, the operator can confirm the region excluded by the processing according to the present embodiment when observing the fourth-dimensional image.

In the first embodiment, the image processing circuitry 16 may set a polygon indicating the drawing initiation surface as a display target when executing surface rendering. Via this process, it is possible to reduce the time required for the drawing process.

In the first embodiment, the image processing circuitry 16 may display the region set as the display target by executing the drawing processing so as to be distinguishable on the tomographic image. Via this process, the operator can confirm from which region of the tomographic image the displayed four-dimensional image has been generated when observing the fourth-dimensional image.

In the first embodiment, the image processing circuitry 16 of the ultrasonic diagnostic apparatus 1 includes the reconstruction region setting function 161, the viewpoint/observation direction setting function 162, the search initiation surface setting function 163, the search axis setting function 164, the drawing initiation surface setting function 165, and the drawing processing function 166. However, the embodiments are not limited thereto. For example, the image processing circuitry 16 may accomplish an edit function by executing an image processing program stored in the internal memory 18.

The edit function is, for example, a function of editing a range where the rendering processing using the drawing initiation surface, which is the processing according to the present embodiment, is to be applied. Specifically, via the edit function, the image processing circuitry 16 sets an editorial ROI to distinguish ranges where the processing according to the present embodiment is applied and not applied. For example, it is assumed that a region where the operator intended to display is set to be a non-display region by applying the processing according to the present embodiment. In this case, the operator sets, via the input interface 111, the editorial ROI that represents a region where the processing according to the present embodiment is not applied on the tomographic image. If the editorial ROI is set, the image processing circuitry 16 displays a second rendering image obtained by the general rendering processing for the region where the editorial ROI is set, and displays a first rendering image obtained by the processing according to the present embodiment for the region where the editorial ROI is not set. FIG. 18 shows an example of the editorial ROI set on the tomographic image.

The editorial ROI may represent a region where the processing according to the present embodiment is to be applied. If the editorial ROI is set, the image processing circuitry 16 displays the first rendering image obtained by the processing according to the present embodiment for the region where the editorial ROI is set, and displays the second rendering image obtained by the general rendering processing for the region where the editorial ROI is not set.

Via the edit function, the range where the processing according to the present embodiment is to be applied can be edited on the tomographic image, thereby the operator can switch the region not displayed on the four-dimensional image display.

The image processing circuitry 16 may accomplish a determination function by executing an image processing program stored in the internal memory 18. The determination function is, for example, a function of determining whether or not the drawing initiation surface or the display region is appropriate.

Specifically, via the determination function, the image processing circuitry 16 defines an evaluation function for determining the appropriateness of the drawing initiation surface and the display region. Upon calculation of the drawing initiation surface in step S25, the image processing circuitry 16 determines the appropriateness of the calculated drawing initiation surface, or the appropriateness of the display region based on the calculated drawing initiation surface, based on the evaluation value calculated by the evaluation function. For example, if the arm region is located in front of the face region, the calculated drawing initiation surface and the display region are spatially discontinuous at the boundary between the arm region and the face region. The image processing circuitry 16 determines the appropriateness of the drawing initiation surface and the display region using the number of voxels in the spatially continuous drawing initiation surface and the display region as the evaluation value. In this case, as the evaluation value is smaller, the image processing circuitry 16 determines the drawing initiation surface and the display region to be appropriate. The image processing circuitry 16 automatically resets the position of the search initiation surface set in step S23, and/or the setting method depending on the appropriateness determination results based on the evaluation value of the evaluation function, which indicate, for example, that the drawing initiation surface or the display region is not appropriate, etc.

The image processing circuitry 16 automatically resets the setting method for the search axis set in step S24, depending on the determination-of-appropriateness results based on the evaluation value of the evaluation function.

Via the determination function, it is determined whether or not the drawing initiation surface or the display region is appropriate, and if it is determined as not appropriate, at least one of the search initiation surface or the search axis is reset so that the image processing circuitry 16 can automatically set a search initiation surface and a search axis desirable for generating an image suitable for observation.

In the first embodiment, in steps S21 to S26 of FIG. 2, the image processing circuitry 16 executes the functions from the reconstruction region setting function 161, to the viewpoint/observation direction setting function 162, to the search initiation surface setting function 163, to the search axis setting function 164, to the drawing initiation surface setting function 165, and to the drawing processing function 166. However, the procedure of the operation of the image processing circuitry 16 is not limited thereto. Each function need not be executed in the order of the reference numbers, and the order of execution can be suitably changed. For example, the search initiation surface may be set after the search axis is set.

The search for the drawing initiation surface by the image processing circuitry 16 described in the first embodiment may affect the region of brain tissues, etc. that may be in the fetal region. The method according to the first embodiment can be used in the following manner in the case where the region of brain tissues, etc. is in the fetal region.

FIG. 19 is a flowchart of another example of the operation when generating rendering image data in which regions unnecessary for observation are deleted by the image processing circuitry 16 shown in FIG. 1.

The image processing circuitry 16 executes the image processing program if an instruction to execute the four-dimensional image display, in which the regions unnecessary for observation have been deleted, is input from the operator. If the image processing program is executed, for example, the reconstruction region setting function 161 is first accomplished. Via the reconstruction region setting function 161, the image processing circuitry 16 sets a reconstruction region based, for example, on an ROI region designated via the input interface 111 (Step S21).

Once the reconstruction region is set, the image processing circuitry 16 executes a region extraction function. Via the region extraction function, the image processing circuitry 16 extracts the boundary between the fetal region and the amniotic fluid region by using, for example, the known region extraction algorithm such as pattern recognition, etc. (step S191). After extracting the boundary between the fetal region and the amniotic fluid region, the image processing circuitry 16 sets the viewpoint, the observation direction, the search initiation surface and the search axis, for example, by steps S22 to S24. The search initiation surface set here is referred to as, for example, a search initiation surface S1 (1) in time phase t=1.

Once the viewpoint, the observation direction, the search initiation surface and the search axis are set, the image processing circuitry 16 executes the drawing initiation surface setting function 165. After executing the drawing initiation surface setting function 165, the image processing circuitry 16 calculates a drawing initiation surface based on a boundary region between the fetal region and the amniotic fluid region obtained by a search along the search axis from the search initiation surface S1 (1) (Step S192). In this case, the image processing circuitry 16 acquires the boundary region between the fetal region and the amniotic fluid region extracted in step S191 by the search along the search axis from the search initiation surface. The drawing initiation surface calculated based on the boundary surface obtained by the region extraction is referred to as, for example, a drawing initiation surface S2 (1) in time phase t=1.

FIG. 20 is a diagram showing an example of a drawing initiation surface S2 (1) calculated based on the boundary surface obtained by a search along the search axis A1 from the search initiation surface S1 (1).

Once the drawing initiation surface S2 (1) is calculated, the image processing circuitry 16, via the drawing processing function 166, executes rendering processing on the volume data along the observation direction from the drawing initiation surface S2 (1) to generate rendering image data (step S26).

For example, if a predetermined period of time has elapsed after the calculation of the drawing initiation surface S2 (1), the image processing circuitry 16 executes the search initiation surface setting function 163. After executing the search initiation surface setting function 163, the image processing circuitry 16 sets a search initiation surface by using the drawing initiation surface S2 (1) (step S193). Specifically, the image processing circuitry 16 sets, as a new search initiation surface, a set of voxels shifted from voxels on the drawing initiation surface S2 (1) by a predetermined distance in the direction of the search initiation surface S1 (1) along the search axis. Via this process, it is possible to set the search initiation surface in the region close to the face surface of the fetus that exceeds the region of brain tissues etc. located within the fetal region. The search initiation surface set here is referred to as, for example, a search initiation surface S1 (2) in time phase t=2. FIG. 21 is a diagram showing a search initiation surface S1 (2) set based on the drawing initiation surface S2 (1).

Once the search initiation surface S1 (2) is set, the image processing circuitry 16 executes the drawing initiation surface setting function 165. After executing the drawing initiation surface setting function 165, the image processing circuitry 16 calculates a drawing initiation surface based on a boundary region between the fetal region and the amniotic fluid region obtained by a search along the search axis from the search initiation surface S1 (2) (Step S194). The drawing initiation surface in step S194 is, for example, calculated by the process similar to step S25. The drawing initiation surface calculated based on the search from the search initiation surface S1 (2) is referred to as, for example, a drawing initiation surface S2 (2) in time phase t=2. FIG. 22 is a diagram showing an example of a drawing initiation surface S2 (2) calculated based on a search from the search initiation surface S1 (2).

Once the drawing initiation surface S2 (2) is calculated, the image processing circuitry 16, via the drawing processing function 166, executes rendering processing on the volume data along the observation direction from the drawing initiation surface S2 (2) to generate rendering image data (step S195).

In the subsequent time phases t=3, 4, . . . , the image processing circuitry 16 is not necessary to calculate a drawing initiation surface. For example, the image processing circuitry 16 may use the drawing initiation surface S2 (2) calculated in t=2 in the subsequent time phases t=3, 4, . . . . The time phase in which the drawing initiation surface is calculated may be discretionarily determined. The drawing initiation surface may be recalculated in a predetermined cycle.

Once the search initiation surface S1 (2) is set, the image processing circuitry 16 calculates a drawing initiation surface by using the search initiation surface S1 (2) unless the fetus greatly moves. For example, if the fetus moves more than a predetermined degree, the image processing circuitry 16 re-executes the process from step S191 of FIG. 19 to set the search initiation surface.

As stated above, the image processing circuitry 16 sets the search initiation surface in the region closer to the face surface of the fetus, and calculates the drawing initiation surface based on the search initiation surface. Via this process, it is possible to efficiently set the drawing initiation surface, which is a surface from which the rendering processing is initiated, between the face of the fetus which is the observation target and an object unnecessary for observation, even if brain tissues, etc. are located in the fetal region. Thus, even if brain tissues, etc. are located in the fetal region, and an arm, an umbilical cord, etc. unnecessary for observation is placed in front of the face of the fetus, the face of the fetus, which is the observation target, can be displayed at high speed.

It has been described that the search initiation surface is set by using the region extraction processing such as pattern recognition, etc.; however, the region extraction processing is need merely be executed once at the time of starting the method, and accordingly, the real time property is not degraded.

In the first embodiment, when the ultrasonic diagnostic apparatus 1 executes the four-dimensional image display, the processing according to the present embodiment is used. However, the processing according to the present embodiment is not limited to be used for executing the four-dimensional image display. For example, the method may be adopted to the two-dimensional image or the three-dimensional image.

In the first embodiment, the face of the fetus is displayed. However, the method can be utilized for a portion of the fetus other than the face. For example, the fetus often bends its legs, and it is difficult to observe a portion between the legs, and to determine the gender. By applying the method to the lower-body of the fetus, a part of the legs that obstructs determination of the gender can be deleted. Thus, the method can be used for effective determination of the gender of the fetus.

In addition, application of the method is not limited to the fetus. For example, the method can be utilized for organs of the circulatory system that have a lumen in which a blood region is included, such as a blood vessel and a heart, etc.

In the first embodiment, the ultrasonic diagnostic apparatus 1 which is an example of the medical image diagnostic apparatus uses the processing according to the present embodiment. However, the medical image diagnostic apparatus using the processing according to the present embodiment is not limited to the ultrasonic diagnostic apparatus 1. The processing according to the present embodiment may be used for any medical image diagnostic apparatus, for example, an X-ray diagnostic apparatus, an X-ray CT (Computed Tomography) apparatus, an MRI (Magnetic Resonance Imaging) apparatus, a SPECT (Single Photon Emission Computed Tomography) apparatus, a PET (Positron Emission computed Tomography) apparatus, a SPECT-CT apparatus in which the SPECT apparatus and the X-ray CT apparatus are integrated, a PET-CT apparatus in which the PET apparatus and the X-ray CT apparatus are integrated, a PET-MRI apparatus in which the PET apparatus and the MRI apparatus are integrated, or a set of these apparatuses.

An example where the processing according to the present embodiment is used by the X-ray diagnostic apparatus will be described below.

(Example of Use in X-Ray Diagnostic Apparatus)

In the example for the ultrasonic diagnostic apparatus 1, the processing according to the present embodiment is utilized, and the fetal region enclosed by the amniotic fluid region is displayed as four-dimensional image display. In the following example, the processing according to the present embodiment is used to display a target that has a lumen such as a stomach, and a large intestine. In this case, an air region within a stomach, a gas region within a large intestine, or a content region such as gastric juices, digests, etc. are defined instead of the amniotic fluid region in the aforementioned example.

The image processing circuitry 16 provided in the X-ray diagnostic apparatus accomplishes the reconstruction region setting function 161, the viewpoint/observation direction setting function 162, the search initiation surface setting function 163, the search axis setting function 164, the drawing initiation surface setting function 165, and the drawing processing function 166, by executing an image processing program stored in internal storage circuitry.

Via the reconstruction region setting function 161, the image processing circuitry 16 receives from the operator a designation of an ROI region relative to a medical image including the stomach displayed on the display 40. The image processing circuitry 16 sets a reconstruction region in the volume data, based on the designated ROI region. FIG. 23 is a diagram showing a reconstruction region set relative to a medical image including a stomach.

Via the viewpoint/observation direction setting function 162, the image processing circuitry 16 receives a designation of a viewpoint and an observation direction when observing, for example, a three-dimensional image or a four-dimensional image. The image processing circuitry 16 sets the designated viewpoint and observation direction. Via the search initiation surface setting function 163, the image processing circuitry 16 sets a search initiation surface at a position farther from the set viewpoint in comparison with the air region which is a non-display region.

Via the search axis setting function 164, the image processing circuitry 16 sets the search axis based, for example, on the observation direction, and the search initiation surface, etc. Via the drawing initiation surface setting function 165, the image processing circuitry 16, for example, calculates a drawing initiation surface based on a boundary region between the gastric wall region and the air region, which is obtained by a search along the search axis from the search initiation surface. Via the drawing processing function 166, the image processing circuitry 16 executes rendering processing on the volume data along the observation direction from the drawing initiation surface to generate rendering image data representing the inner wall region of the stomach.

Figure 24:
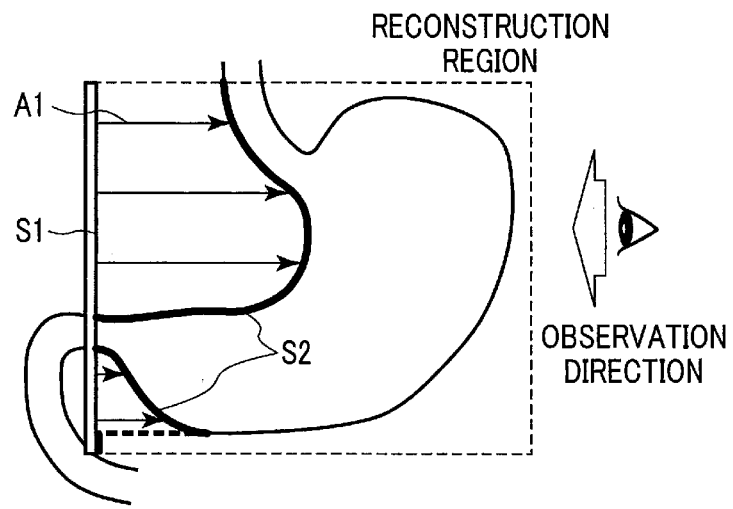
FIG. 24 is a schematic drawing showing a display region in the reconstruction region set in FIG. 23.
Figure 25:
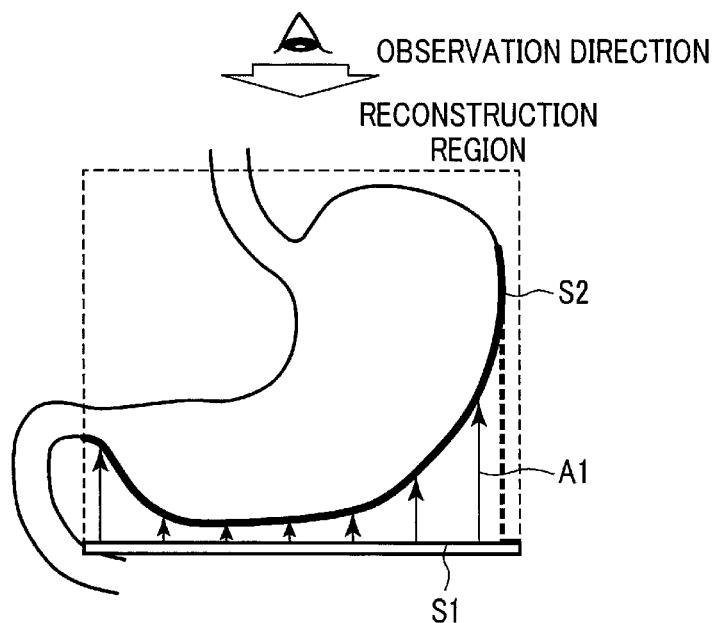
FIG. 25 is a schematic drawing showing a display region in the reconstruction region set in FIG. 23.

FIGS. 24 and 25 each are a schematic drawing showing a display region in the reconstruction region set in FIG. 23. FIG. 24 shows a display region in which the viewpoint is set at the greater curvature side of the stomach, and the observation direction is set from the greater curvature side to the lesser curvature side. In FIG. 24, the search initiation surface is set to use a cross section of the boundary at the pylorus side of the reconstruction region, and the search axis is set to be parallel to the observation direction and opposite to the observation direction. The drawing initiation surface is calculated based on the boundary region between the gastric wall region and the air region, and the rendering processing is executed on the volume data along the observation direction from the drawing initiation surface to generate rendering image data representing the inner wall region of the pyloric antrum, the lesser curvature, and the esophagus, etc.

FIG. 25 shows a display region in which the viewpoint is set at the esophagus side of the stomach, and the observation direction is set from the esophagus side to the pyloric antrum side. In FIG. 25, the search initiation surface is set to use a cross section of the boundary at the pyloric antrum side of the reconstruction region, and the search axis is set to be parallel to the observation direction and opposite to the observation direction. The drawing initiation surface is calculated based on the boundary region between the gastric wall region and the air region, and the rendering processing is executed on the volume data along the observation direction from the drawing initiation surface to generate rendering image data representing the inner wall region of the pyloric antrum, the greater curvature of the stomach body.

In the present example, the observation target is set to be an organ of the circulatory system that has a lumen in which the air region, the gas region, or the content region is included, such as the large intestine and the stomach, etc.; however the present example is not limited to the organs of the circulatory system. For example, the example can be applied for a blood vessel and a heart, which are organs having a lumen. In this case, a blood region can be used instead of the air region, the gas region, or the content region. Any regions extracted by using the known region extraction algorithm can of course be used instead of the air region, the gas region, or the content region.

Second Embodiment

In the first embodiment, the medical image diagnostic apparatus such as the ultrasonic diagnostic apparatus 1 is described. In the second embodiment, a medical image processing apparatus 2 that is installed in a hospital information system will be described.

Figure 26:
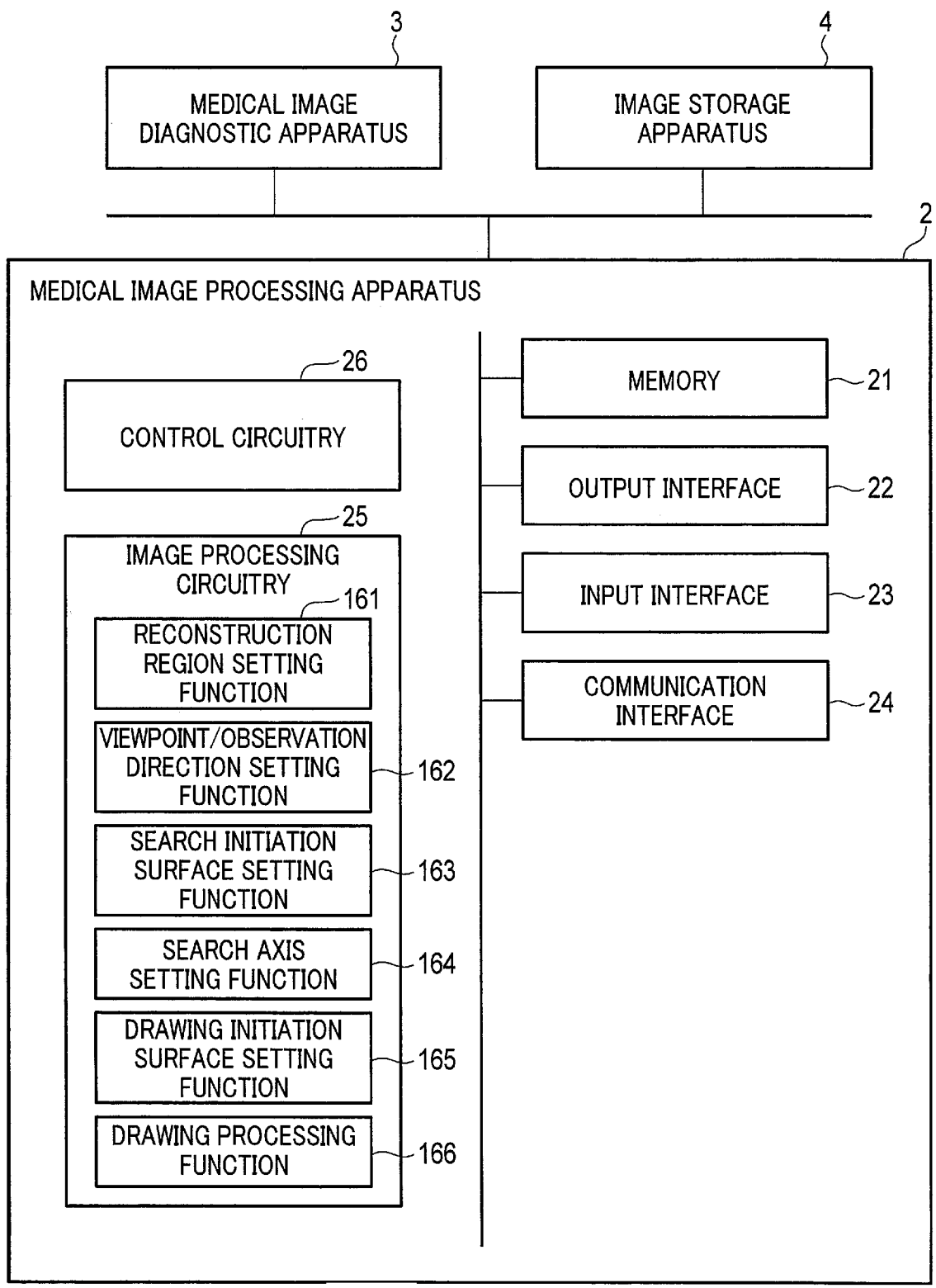
FIG. 26 is a drawing showing an example of a medical information system including a medical image processing apparatus according to the second embodiment.

FIG. 26 is a drawing showing an example of a medical information system including a medical image processing apparatus 2 according to the second embodiment. The medical information system shown in FIG. 26 includes the medical image processing apparatus 2, a medical image diagnostic apparatus 3, and an image storage apparatus 4. The medical image processing apparatus 2, the medical image diagnostic apparatus 3, and the image storage apparatus 4 are directly or indirectly connected so as to be communicable to each other via, for example, a hospital LAN (Local Area Network) installed in a hospital. For example, if the image storage apparatus 4 constitutes a PACS, the medical image processing apparatus 2, the medical image diagnostic apparatus 3, and the image storage apparatus 4 mutually transmit or receive, for example, medical image data, in accordance with the DICOM standards.

The medical image diagnostic apparatus 3 is an apparatus that generates medical image data by imaging a subject. The medical image diagnostic apparatus 3 transmits generated medical image data to the medical image processing apparatus 2 and the image storage apparatus 4.

The image storage apparatus 4 is a database that stores medical image data. The image storage apparatus 4, for example, stores medical image data generated by the medical image diagnostic apparatus 3 in storage circuitry provided inside of the image storage apparatus 4.

The medical image processing apparatus 2 is an apparatus that executes image processing on the medical image data generated by the medical image diagnostic apparatus 3, or medical image data read from the image storage apparatus 4. The medical image processing apparatus 2 shown in FIG. 26 includes a memory 21, an output interface 22, an input interface 23, a communication interface 24, image processing circuitry 25, and control circuitry 26.

The memory 21 is implemented, for example, by a semiconductor memory element, such as a RAM (Random Access Memory) and a flash memory, a hard disk, and an optical disk, etc. The memory 21 stores, for example, a program, etc. by which the image processing circuitry 25 and the control circuitry 26 accomplish their functions.

The output interface 22 is connected to the control circuitry 26, and outputs a signal supplied from the control circuitry 26. The output interface 22 is implemented, for example, by a display. The display displays, for example, a medical image based on the medical image data, GUI for receiving various types of operations from a user, etc., based on an instruction from the control circuitry 26.

The input interface 23 receives various types of input operations from the user, converts the received input operations to an electric signal, and outputs the electric signal to the control circuitry 26.

The communication interface 24, for example, is connected to a hospital network. The communication interface 24, for example, receives medical image data, etc., from the medical image diagnostic apparatus 3 and the image storage apparatus 4 via the hospital network.

The image processing circuitry 25 is a processor that executes predetermined image processing on medical image data such as two-dimensional image data or volume data, etc. Specifically, the image processing circuitry 25, for example, executes an image processing program stored in the memory 21 and accomplishes a function corresponding to the program. The image processing circuitry 25, for example, has the reconstruction region setting function 161, the viewpoint/observation direction setting function 162, the search initiation surface setting function 163, the search axis setting function 164, the drawing initiation surface setting function 165, and the drawing processing function 166.

The image processing circuitry 25 sets a viewpoint and an observation direction relative to the ultrasonic image data such as volume data, via these functions. The image processing circuitry 25 sets a search initiation surface at a position farther away from the set viewpoint in comparison with a region unnecessary for observation that obstructs the observation of the observation target in the ultrasonic image data. The image processing circuitry 25 sets a search axis from the set search initiation surface toward the viewpoint. The image processing circuitry 25 searches for a region which satisfies a predetermined requirement along the set search axis from the search initiation surface, and calculates a drawing initiation surface based on the search results. The image processing circuitry 25 then executes drawing processing from the calculated drawing initiation surface toward the observation direction to generate display image data. Via this processing, it is possible to efficiently set a drawing initiation surface which is a surface from which the rendering processing is initiated between the observation target and an object unnecessary for the observation. Thus, even if a region that obstructs the observation is located in front of the observation target, the observation target can be displayed while deleting the region.

For example, in the case of observing an inner wall of a stomach, a wall located opposite the inner wall to be observed obstructs the observation. According to this method, the inner wall to be observed can be displayed while a part of the inner wall that obstructs the observation is set to be non-displayed.

According to at least one embodiment described above, even if an object unnecessary for observation is located in front of the observation target, the medical image diagnostic apparatus and the medical image processing apparatus can perform four-dimensional image display of only the observation target without the need for executing slow calculations.

The term "processor" used in the above descriptions of the embodiment means, for example, circuitry such as a CPU (Central Processing Unit), a GPU (Graphics Processing Unit), an ASIC (Application Specific Integrated Circuit), or a programmable logic device (for example, an SPLD (Simple Programmable Logic Device), a CPLD (Complex Programmable Logic Device), or an FPGA (Field Programmable Gate Array), etc. A processor implements functions by reading and executing a program stored in the storage circuitry. Instead of storing a program on the memory circuitry, the program may be directly integrated into the circuitry of the processor. In this case, the function is activated by reading and executing the program integrated into the circuitry. Each processor of the above embodiment is not limited to be configured as single circuitry, but may include a plurality of units of independent circuitry, in order to implement the functions. Furthermore, a plurality of constituent elements shown in FIG. 1 may be integrated into one processor to realize the function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image diagnostic apparatus comprising:
processing circuitry configured to:
set a viewpoint and an observation direction to medical image data, the viewpoint being a position to observe the medical image data, and the observation direction being a direction toward the medical image data from the viewpoint;
search the medical image data for a region to be displayed from a search initiation surface, the search initiation surface being farther away from the viewpoint along the observation direction in comparison with a region obstructing the region to be displayed;
calculate a drawing initiation surface based on a result of the search; and
generate display image data by drawing the region to be displayed from the drawing initiation surface in the observation direction.

2. The medical image diagnostic apparatus according to claim 1, wherein:
the region obstructing the region to be displayed is a hand region of a fetus.

3. The medical image diagnostic apparatus according to claim 1, wherein:
the processing circuitry is configured to:
extract a region representing a predetermined structure from a tomographic image; and
set a cross section corresponding to a line passing through a point within the extracted region as the search initiation surface.

4. The medical image diagnostic apparatus according to claim 1, wherein:
the processing circuitry is configured to set a region in the medical image data, and to set a search initiation surface passing through the region.

5. The medical image diagnostic apparatus according to claim 4, wherein:
the processing circuitry is configured to set the search initiation surface at a position farther away from the viewpoint in comparison with a region unnecessary for observation in the medical image data, and not outside a boundary of the region farther away from the viewpoint.

6. The medical image diagnostic apparatus according to claim 1, wherein:
the processing circuitry is configured to:
set a plurality of search initiation surfaces, each corresponding to the search initiation surface; and
initiate a search for the region to be displayed from a search initiation surface closer to the viewpoint among the plurality of search initiation surfaces.

7. The medical image diagnostic apparatus according to claim 1, wherein:
the processing circuitry is configured to set a search initiation surface in a current time phase by using a search initiation surface set in a different time phase.

8. The medical image diagnostic apparatus according to claim 1, wherein:
the processing circuitry is configured to use a drawing initiation surface calculated in a different time phase as a drawing initiation surface in a current time phase.

9. The medical image diagnostic apparatus according to claim 1, wherein:
the processing circuitry is configured to:
extract a display region; and
set a search initiation surface based on the extracted display region.

10. The medical image diagnostic apparatus according to claim 1, wherein:
the processing circuitry is configured to:
calculate the drawing initiation surface using a first opacity curve in which an opacity of a display region is set to be low, and an opacity of the region obstructing the region to be displayed is set to be high with a predetermined contrast; and
execute the drawing processing by using a second opacity curve in which the opacity of the display region is set to be high, and the opacity of the region obstructing the region to be displayed is set to be low with a contrast higher than the first opacity curve.

11. The medical image diagnostic apparatus according to claim 1 wherein:
the processing circuitry is configured to superimpose a region corresponding to the search initiation surface with display image data generated by the drawing processing.

12. The medical image diagnostic apparatus according to claim 1 wherein:
the processing circuitry is configured to superimpose a region corresponding to the drawing initiation surface with display image data generated by the drawing processing.

13. The medical image diagnostic apparatus according to claim 1 wherein:
the processing circuitry is configured to superimpose the generated display image data with a differential image between the generated display image data and display image data generated by drawing from the viewpoint toward the observation direction.

14. The medical image diagnostic apparatus according to claim 1 wherein:
the processing circuitry is configured to set a polygon representing the drawing initiation surface as a display target.

15. The medical image diagnostic apparatus according to claim 1 wherein:
the processing circuitry is configured to display a region in the medical image data set to be a display target by drawing so as to be distinguishable on the tomographic image.

16. The medical image diagnostic apparatus according to claim 1 wherein:
the processing circuitry is configured to edit a range of the medical image data to be drawn by using the drawing initiation surface.

17. The medical image diagnostic apparatus according to claim 1 wherein:
the processing circuitry is configured to determine whether or not the drawing initiation surface or the display image data is appropriate.

18. A medical image diagnostic apparatus comprising:
processing circuitry configured to:
set a viewpoint and an observation direction relative to medical image data;
search for a region that satisfies a predetermined requirement from a search initiation surface set at a predetermined position farther away from the viewpoint in comparison with a region in the medical image data in a direction toward the viewpoint;
calculate a drawing initiation surface using a result of the search and a first opacity curve in which an opacity of a display region is set to be low, and an opacity of a non-display region is set to be high with a predetermined contrast; and
generate display image data by executing drawing processing from the drawing initiation surface in the observation direction using a second opacity curve in which the opacity of the display region is set to be high, and the opacity of the non-display region is set to be low with a contrast higher than the first opacity curve.

19. An image processing method comprising:
setting a viewpoint and an observation direction to medical image data, the viewpoint being a position to observe the medical image data, and the observation direction being a direction toward the medical image data from the viewpoint;
searching the medical image data for a region to be displayed from a search initiation surface, the search initiation surface being farther away from the viewpoint along the observation direction in comparison with a region unnecessary for observation in the medical image data in a direction toward the viewpoint;
calculating a drawing initiation surface based on a result of the search; and
generating display image data by drawing from the drawing initiation surface in the observation direction.

* * * * *